(12) United States Patent
Steffan et al.

(10) Patent No.: US 7,598,286 B2
(45) Date of Patent: Oct. 6, 2009

(54) [(1H-INDAZOL-3-YL)METHYL]PHENOLS AND (HYDROXYPHENYL)(1H-INDAZOL-3-YL) METHANONES

(75) Inventors: Robert John Steffan, Langhorne, PA (US); Edward Martin Matelan, Royersford, PA (US)

(73) Assignee: Wyeth, Madison, NJ (US)

( * ) Notice: Subject to any disclaimer, the term of this patent is extended or adjusted under 35 U.S.C. 154(b) by 538 days.

(21) Appl. No.: 11/260,127

(22) Filed: Oct. 27, 2005

(65) Prior Publication Data

US 2006/0106084 A1  May 18, 2006

Related U.S. Application Data

(60) Provisional application No. 60/623,976, filed on Nov. 1, 2004.

(51) Int. Cl.
A61K 31/416 (2006.01)
(52) U.S. Cl. .......................... 514/406; 514/403; 514/23; 548/361.1; 536/17.4
(58) Field of Classification Search ................. 514/406, 514/403, 23; 548/361.1; 536/17.4
See application file for complete search history.

(56) References Cited

U.S. PATENT DOCUMENTS 5,691,362 A   11/1997   McCormick et al. ........ 514/339

FOREIGN PATENT DOCUMENTS

| EP | 0 358 903 A2 | 3/1990 |
|---|---|---|
| EP | 0 538 000 A1 | 4/1993 |
| EP | 0 562 832 A1 | 9/1993 |
| EP | 0 671 390 A2 | 9/1995 |
| WO | 93/13099 A1 | 7/1993 |
| WO | 95/15758 A1 | 6/1995 |
| WO | 98/09961 A1 | 3/1998 |
| WO | 98/43969 A1 | 10/1998 |
| WO | 2004/031159 A1 | 4/2004 |

OTHER PUBLICATIONS

Adams, M. R. et al., "Inhibition of Coronary Artery Atherosclerosis by 17-beta Estradiol in Ovariectomized Monkeys," *Arterio.*, 1990, 10(6), 1051-1057.
Alexander et. al., "Initiation of Hormone Replacement Therapy After Acute Myocardial Infarction Is Associated With More Cardiac Events During Follow-Up," *J. Am. Coll. Cardio.*, 2001, 38, 1-7.
Bauer M. A., Herrmann F., "Interleukin-6 in clinical medicine," *Ann. Hematol.*, 1991, 62, 203-210.
Boulton, B. E. et al., "Kinetics, Stoichiometry and Mechanism in the Bromination of Aromatic Heterocycles. III Aqueous Bromination of Indazole," *Aust. J. Chem.*, 1974, 27, 2343-2347.
Cefalu, W., "The Use of Hormone Replacement Therapy in Postmenopausal Women with Type 2 Diabetes," *J Womens Health & Gender-based Med.*, 2001, 10(3), 241-255.

Cercek, B. et al., "Nuclear factor-κB Activity and arterial response to balloon injury," *Atherosclerosis* 131, 59-66 (1997).
Chandrasekar, B. et al. "Ischemia-Reperfusion of Rat Myocardium Activates Nuclear Factor-κB and Induces Neutrophil Infiltration Via Lipopolysaccharide-Induced CXC Chemokine," *Circulation*, 2001 103, 2296-2302.
Collot, V. et al., "Heck cross-coupling reaction of 3-iodoindazoles with methyl acrylate: a mild and flexible strategy to design 2-azatryptamines," *Tetrahedron Letters*, 2000, 41, 4363.
Collot, V. et al., "Suzuki-Type Cross-Coupling Reaction of 3-Iodoindazoles with Aryl Boronic Acids: a General and Flexible Route to 3-Arylindazoles," *Tetrahedron*, 1999, 55, 6917.
Collot, V. et al., "First combined selective N- and C-arylations with boronic acids: application to the synthesis of 1,3-diarylindazoles," *Tetrahedron Letters*, 2000, 41, 9053-9057.
Cuzzocrea, S. et al., "17β-Estradiol Antiinflammatory Activity in Carrageenan-Induced Pleurisy," *Endocrinology*, 2000, 141, 1455-1463.
Delyani, J. A. et al., "Protection from Myocardial Reperfusion Injury by Acute Administration of 17 β-Estradiol," *J. Molec. Cell. Cardiol.*, 1996, 28, 1001-1008.
Dietrich, H. et al., "Mouse Model of Transplant Arteriosclerosis," *Arterioscler. Thromb. Vasc. Biol.*, 2000, 20, 343-352.
Dubal, D. B. et al., "Estradiol Modulates bcl-2 in Cerebral Ischemia: A Potential Role for Estrogen Receptors," *J. Neurosci.*, 1999, 19, 6385-6393.
Dubal, D. B. et al., "Estrogen receptor α, not β, is a critical link in estradiol-mediated protection against brain injury," *PNAS, USA*, 2001, 98, 1952-1957.

(Continued)

*Primary Examiner*—Kamal A Saeed
*Assistant Examiner*—Valerie Rodriguez-Garcia
(74) *Attorney, Agent, or Firm*—Pepper Hamilton LLP

(57) ABSTRACT

This invention provides anti-inflammatory agents of formula I, having the structure

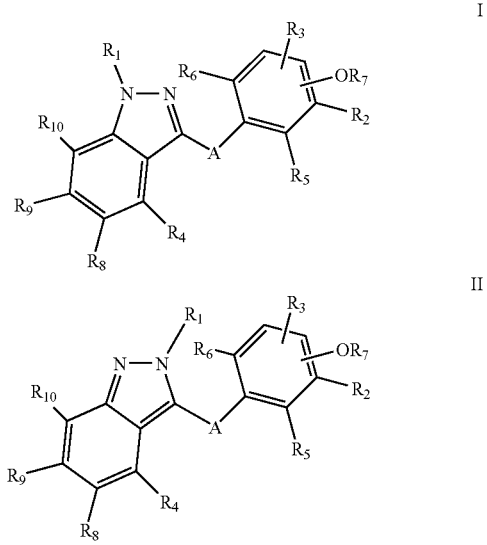

wherein A and $R_1$-$R_{10}$ are as defined in the specification, or a N-oxide thereof or a pharmaceutically acceptable salt thereof or a prodrug thereof.

9 Claims, No Drawings

OTHER PUBLICATIONS

Felson, D. T. et al., "The effects of estrogen on osteoarthritis," *Curr Opinion Rheum*, 1998, 10, 269-272.

Fludzinski, P. et. al., "Indazoles as indole bioisosteres: synthesis and evaluation of the tropanyl ester and amide of indazole-3-carboxylate as antagonists at the serotonin 5HT3 receptor," *J. Med. Chem*, 1987, 30(9), 1535-1537.

Grodstein F. et. al., "Postmenopausal Hormone Use and Secondary Prevention of Coronary Events in the Nurses' Health Study," *Ann. Int. Med*, 2001, 135, 1-8.

Grodstein, F. et. al., "A Prospective, Observational Study of Postmenopausal Hormone Therapy and Primary Prevention of Cardiovascular Disease," *Ann. Int. Med.*, 2000, 133, 933-41.

Harada, H. et al., "Development of potent serotonin-3 (5-HT3) receptor antagonists. II. Structrue-activity relationships of N-(1-benzyl-4-methylhexahydro-1H-1,4-diazepin-6-yl)carboxamides," *Chem. Pharm. Bull.*, 1995, 43(11), 1912-1930.

Hulley, S. et. al., "Randomized Trial of Estrogen Plus Progestin for Secondary Prevention of Coronary Heart Disease in Postmenopausal Women," *J. Am. Med. Assoc.*, 1998, 280, 605-13.

Ishiyama, H. et al., "Palladium-Catalyzed Carbonylative Cross-Coupling Reaction of Arylboronic Acids with Aryl Electrophiles: Synthesis of Biaryl Ketones," *J. Org. Chem.*, 1998, 63, 4726-4731.

Izumi, T. et al., "Blockade of the natriuretic peptide receptor guanylyl cyclase-A inhibits NF-κB activation and alleviates myocardial ischemia/reperfusion injury," *J. Clin. Invest.*, 2001, 108, 203-213.

Kadokami, T. et al., "Anti-Tumor Necrosis Factor-α Antibody Limits Heart Failure in a Transgenic Model," *Circulation*, 2001, 104, 1094-1097.

Karas, R. H. et al., "Effects of Estrogen on the Vascular Injury Response in Estrogen Receptor α,β (Double) Knockout Mice," *Circ. Res.*, 2001, 89, 534-539.

Kurebayashi S. et. al., "Characterization of Mechanisms of Interleukin-6 Gene Repression by Estrogen Receptor," *J. Steroid Biochem. Molec. Biol.*, 1997, 60, 11-17.

Lin, C. C. et.al., "Pulmonary function changes and increased Th-2 cytokine expression and nuclear factor kB activation in the lung after sensitization and allergen challenge in brown Norway rats," *Immunol. Lett.*, 2000, 73, 57-64.

Lou, H. et al., "Inhibition of Transplant Coronary Arteriosclerosis in Rabbits by Chronic Estradiol Treatment Is Associated With Abolition of MHC Class II Antigen Expression," *Circulation*, 1996, 94, 3355-3361.

Lundeen, S. G. et al., "Rat uterine complement C3 expression as a model for progesterone receptor modulators: characterization of the new progestin trimegestone," *J. Steroid Biochem Biol.*, 2001, 78, 137-143.

Mankin, H. J. et al., "Biochemical and Metabolic Abnormalities in Articular Cartilage from Osteo-Arthritic Human Hips," *Journal of Bone & Joint Surgery*—American vol. 53, 523-537 (1971).

Merchenthaler, I. et al., "The effect of estrogens and antiestrogens in a rat model for hot flush," *Maturitas*, 1998, 30, 307-316.

Nahm, S. et al., "N-Methoxy-N-Methylamides as Effective Acylating Agents," *Tetrahedron Lett.* 1981, 22(39), 3815-3818.

Nathan, L. et. al., "Estradiol Inhibits Leukocyte Adhesion and Transendothelial Migration in Rabbits In Vivo," *Circ. Res.*, 1999, 85, 377-385.

Pelletier et al., "Osteoarthritis, an Inflammatory Disease," *Arthr. & Rheum.*, 2001, 44, 1237-1247.

Poole, A. R et al., "Rheumatoid-Like Joint Lesions in Rabbits Injected Intravenously with Bovine Serum," *International Archives of Allergy & Applied Inmunology*, 1977, 54, 97-113.

Prokai, L. et al., "Synthesis and Biological Evaluation of 17β-Alkoxyestra-1,3,5(10)-trienes as Potential Neuroprotectants Against Oxidative Stress," *J. Med. Chem.*, 2001, 44, 110-114.

Reis et. al., "Estrogen Is Associated With Improved Survival in Aging Women With Congestive Heart Failure: Analysis of the Vesnarinone Studies," *J. Am. Coll. Cardio.*, 2000, 36, 529-33.

Robertson, D. W. et al., "Synthesis and biochemical evaluation of tritium-labeled 1-methyl-N-(8-methyl-8-azabicyclo[3.2.1]oct-3-yl)-1H-indazole-3-carboxa mide, a useful radioligand for 5HT3 receptors," *J. Med. Chem.*, 1990, 23, 3176-3181.

Roth, A. et. al., "Phytoestrogen Kaempferol (3,4',5,7-Tetrahydroxylflavone) Protects PC12 and T47D Cells From β-Amyloid-Induced Toxicity," *J. Neurosci. Res.*, 1999, 57, 399-404.

Schonknecht, P. et. al., "Reduced cerebrospinal fluid estradiol levels are associated with increased β-amyloid levels in female patients with Alzheimer's disease," *Neurosci. Lett.*, 2001, 307, 122-124.

Shughrue, P. J. et al., "Regulation of Progesterone Receptor Messenger Ribonucleic Acid in the Rat Medial Preoptic Nucleus by Estrogenic and Antiestrogenic Compounds: An in Situ Hybridization Study," *Endocrinology*, 1997, 138, 5476-5484.

Shutske, G. M. et al., "Heterocyclic Oxyacetic Acid Diuretics: Indazole, Benzisothiazole, and Benzisothiazole 1,1-Dioxide Analogues of [[7-Chloro-3-(2-fluorophenyl)-1,2-benzisoxazol-6-yl]oxy]acetic Acid," *J. Med. Chem.*, 1963, 26(9), 1307-1311.

Smirnoff, P. et al., "The Protective Effect of Estrogen Against Chemically Induced Murine Colon Carcinogenesis Is Associated With Decreased CpG Island Methylation and Increased mRNA and Protein Expression of the Colonic Vitamin D Receptor," *Oncology Research*, 1999, 11, 255-264.

Stetson, S. J. et al., "Cardiac Hypertrophy After Transplantation Is Associated With Persistent Expression of Tumor Necrosis Factor-α," *Circulation*, 2001, 104, 676-681.

Sullivan, T. R. et al. "Estrogen Inhibits the Response-to-Injury in a Mouse Carotid Artery Model," *J. Clin. Invst.*, 1995, 96, 2482-8.

Wallen, W. J. et al., "Gender-Differences in Myocardial Adaptation to Afterload in Normotensive and Hypertensive Rats," *Hypertension*, 2000, 36, 774-779.

Welch, W. M. et al., "A Novel Synthesis of 3-Substituted Indazole Derivatives," *Synthesis* 1992, 937-939.

Yagi, K., "Short Communications. A Simple Fluorometric Assay for Lipoperoxide in Blood Plasma," *Biochemical Medicine*, 1976, 15, 212-216.

Yokoseki, O. et al., "*cis* Element Decoy Against Nuclear Factor-κB Attenuates Development of Experimental Autoimmune Myocarditis in Rats," *Circ. Res.*, 2001, 89, 899-906.

Yoshida, N. et al., "5-HT3 receptor antagonist effects of DAT-582, (R) enantiomer of AS-5370," *European Journal of Pharmacology*, 1992, 216(3), 435-440.

Yoshida, T. et al., "Practical Synthesis of 1H-Indazole-3-Carboxylic Acid and its Derivatives," *Heterocycles*, 1996, 43(12), 2701-2712.

Yuan et al., "Reversal of Obesity-and Diet-Induced Insulin Resistance with Salicylates or Targeted Disruption of *Ikk*β," *Science*, 2001, 293, 1673-1677.

Zaulyanov, L. L. et al., "Glutamate Receptor Requirement for Neuronal Death from Anoxia-Reoxygenation: An in Vitro Model for Assessment of the Neuroprotective Effects of Estrogens," *Cellular & Molecular Neurobiology*, 1999, 19, 705-718.

Database CAPLUS, Chemical Abstracts Service, Columbus, Ohio, US, 1976, -XP00230889, Retrieved from STN, Database Accession No. 1976:523913 & JP 50157363 A, Dec. 19, 1975.

Hari, Y. et al., "New Synthesis of 3-Substituted Indazoles from 3-Trimethylsilylindazole," *Synthesis*, Jun. 2004, 8, 1183-1186, XP002380817.

Database Registry [Online] Chemical Abstracts Service, Columbus, Ohio, US; 2002, XP002380890, Retrieved from STN, Database Accession No. 405269-14-9, abstract.

Database Registry [Online] Chemical Abstracts Service, Columbus, Ohio, US; 2002, XP002380891, Retrieved from STN, Database Accession No. 402603-97-8, abstract.

Clark, B. J. et al., "Synthesis of 4-Arylmethyl-1,2,3-benzotriazines," *J. Chem. Research (S)*, London, GB, 1981, 10, 324-325, XP009055385.

Strohmeier, J. et al., "Synthesis and Estrogen Receptor Affinity of 2,3-Diarylindoles," *Archiv Der Pharmazie, VCH Verlagsgesellschaft MBH*, Weinheim, DE, 1987, 320, 407-417, XP002976869.

Wermuth, C. G. et al., "Molecular Variations Based on Isosteric Replacements," *Practice Of Medicinal Chemistry*, 1996, 203-237, XP002190259.

Burger, A., (Ed.), Jucker E., "Isosterism and bioisosterism in drug design," *Progress In Drug Research. Fortschritte Der Arneimettelforschung. Progres Des Recherches Pharmaceutiques*, Basel, Birkhauser Verlag, CH, vol. 37, 1991, 287-371, XP002096229.

[(1H-INDAZOL-3-YL)METHYL]PHENOLS AND (HYDROXYPHENYL)(1H-INDAZOL-3-YL) METHANONES

RELATED APPLICATIONS

This application claims the benefit of U.S. Provisional Application No. 60/623,976 filed on Nov. 1, 2004 This application is incorporated by reference herein in its entirety.

FIELD OF THE INVENTION

This invention concerns [(1H-indazol-3-yl)methyl]phenol and (hydroxyphenyl)(1H-indazol-3-yl)methanone compounds, their use, for example, as antiinflammatory agents, and their preparation.

BACKGROUND OF THE INVENTION

The ability of ligands for the estrogen receptor to inhibit inflammatory gene expression causing a reduction of cytokines, chemokines, adhesion molecules and inflammatory enzymes provides a means to treat the inflammatory component of diseases such as atherosclerosis, myocardial infarction (MI), congestive heart failure (CHF), inflammatory bowel disease and arthritis. Other potential therapeutic indications for these type of molecules include type II diabetes (Cefalu, *J Womens Health & Gender-based Med.* 2001, 10, 241 & Yuan et al., *Science,* 2001, 293, 1673), osteoarthritis (Pelletier et al., *Arthr. & Rheum.,* 2001, 44:1237 and Felson et al., *Curr Opinion Rheum,* 1998, 10, 269) asthma (Chin-Chi Lin et. al., *Immunol. Lett.,* 2000, 73, 57), Alzheiemer's disease (Roth, A. et. al., *J. Neurosci. Res.,* 1999, 57, 399) and autoimmune diseases such as multiple sclerosis and rheumatiod arthritis.

A common component of these chronic inflammatory conditions is polymorphonuclear leukocyte and monocyte infiltration into the site of damage through increased expression of cytokines and adhesion molecules responsible for their recruitment. Overproduction of the cytokine interleukin (IL-6) has been associated with states of chronic inflammation (Bauer M. A., Herrmann F., *Ann. Hematol.,* 1991, 62, 203). Synthesis of the IL-6 gene is induced by the transcription factor nuclear factor κB (NF-κB). Interference at this step in the inflammatory process can effectively regulate the uncontrolled proliferative process that occurs in these chronic conditions.

In endothelial cells, 17β-estradiol (E2) inhibits IL-1β induced NF-κB reporter activity and IL-6 expression in an ER dependent fashion (Kurebayashi S. et. al., *J. Steroid Biochem. Molec. Biol.,* 1997, 60, 11). This has been said to correlate with anti-inflammatory action of E2 in vivo as confirmed in different animal models of inflammation. In models of atherosclerosis, E2 was shown to protect endothelial cell integrity and function and to reduce leukocyte adhesion and intimal accumulation (Adams, M. R. et al., *Arterio.,* 1990, 1051, Sullivan, T. R. et al. *J. Clin. Invst.* 1995, 96, 2482, Nathan, L. et. al., *Circ. Res.,* 1999, 85, 377). Similar effects of estrogen on the vascular wall have also been demonstrated in animal models of myocardial infarction (Delyani, J. A. et al., *J. Molec. Cell. Cardiol.,* 1996, 28, 1001) and congestive heart failure. Clinically, estrogen replacement therapy (ERT) has been demonstrated to reduce the risk of mortality in patients with both CHF (Reis et. al., *J. Am. Coll. Cardio.,* 2000, 36, 529) and MI (Grodstein, F. et. al., *Ann. Int. Med.,* 2000, 133, 933, Alexander et. al., *J. Am. Coll. Cardio.,* 2001, 38, 1 and Grodstein F. et. al., *Ann. Int. Med,* 2001, 135,1). In ERT, clinical studies demonstrated an influence of E2 on the decrease in the production. of β-amyloid 1-42 (Aβ42), a peptide central for the formation of senile plaques in Alzheimer's disease (Schonknecht, P. et. al., *Neurosci. Lett.,* 2001, 307, 122).

17-β-estradiol, however, also strongly stimulates creatine kinase expression. Thus, in ERT some potential unwanted side effects, such as an increase risk of cardiovascular events in the first year of use, have been demonstrated (Hulley, S. et. al., *J. Am. Med. Assoc.,* 1998, 280, 605) as well as proliferative effects on uterine and breast tissue.

The ligands for the estrogen receptor described herein were designed to lack these potential side effects while remaining an effective treatment for chronic inflammatory conditions.

SUMMARY OF THE INVENTION

This invention provides [(1H-indazol-3-yl)methyl]phenol and (hydroxyphenyl)(1H-indazol-3-yl)methanone compounds that find use as, for example, anti-inflammatory estrogenic agents. In certain embodiments, such compounds are of formula I or II:

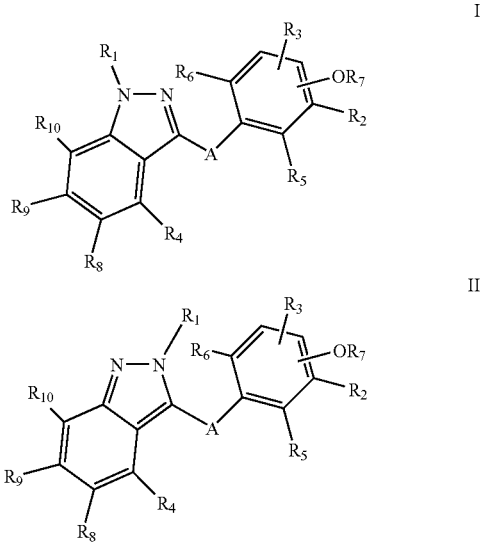

and pharmaceutically acceptable salts thereof;

wherein
A is (C=O), CHOH, C(OH)R or CR'R";
R, R' and R" are each, independently, H, alkyl, aralkyl or aryl;
$R_1$ is hydrogen, lower alkyl, cycloalkyl, alkenyl, cycloalkenyl, heteroaryl, aryl or aralkyl;
$R_2$, $R_3$, $R_5$, and $R_6$ are each, independently, hydrogen, hydroxy, lower alkyl, alkoxy or halogen;
$R_4$, $R_8$, $R_9$, $R_{10}$, are each, independently, hydrogen, lower alkyl, hydroxy, alkoxy, aralkoxy, halogen, $CF_3$, aryl, aralkyl, heteroaryl or $COOR_{11}$;
$R_7$ is hydrogen, alkyl, —(C=O)$R_{16}$, —S(O)$_2R_{17}$, —S(O)$_2$N($R_{18}$)($R_{19}$) or D-glucuronidate;
$R_{11}$ is hydrogen, lower alkyl, aryl, or aralkyl;
$R_{16}$ is alkyl, aralkyl or aryl;
$R_{17}$ is alkyl, aryl, heteroaryl, alkenyl, cycloalkenyl, or alkynyl;
$R_{18}$ and $R_{19}$ are, independently, hydrogen, alkyl, alkenyl, alkynyl, cycloalkyl, monofluoroalkyl, perfluoroalkyl, aryl, arylalkyl, cycloalkenyl, heteroaryl, heteroarylalkyl, hydroxy-($C_2$-$C_6$)alkyl, alkoxyalkyl, alkylthioalkyl, carbonyl, acyl, alkoxycarbonyl, —C(O)$NH_2$, alkylaminocarbonyl, dialkylaminocarbonyl, alkylaminoalkyl, or dialkylaminoalkyl;

or $R_{18}$ and $R_{19}$ are taken together with the nitrogen atom to which they are attached to form a saturated, unsaturated or partially saturated $C_4$-$C_6$ carbon ring;

or a pharmaceutically acceptable salt thereof or a prodrug thereof.

In another aspect, the invention is drawn to pharmaceutical compositions that comprise one or more compounds of the invention and a pharmaceutically acceptable carrier.

In yet other aspects, the invention concerns methods of treating or inhibiting chronic inflammatory disease in a mammal in need thereof, which comprise administering to said mammal an effective amount of a compound of the invention.

Such diseases include rheumatoid arthritis, spondyloarthropathies, osteoarthritis, psoriatic arthritis, juvenile arthritis, inflammatory bowel disease, Crohn's disease, ulcerative colitis, indeterminate colitis, psoriasis, asthma and chronic obstructive pulmonary disease.

The invention is also directed to methods of treating or inhibiting stroke, ischemia, or reperfusion injury in a mammal in need thereof, which comprise administering to said mammal an effective amount of a compound of the invention. In other embodiments, the invention concerns methods of lowering cholesterol, triglycerides, Lp(a), and LDL levels; inhibiting or treating hypercholesteremia, hyperlipidemia, cardiovascular disease, atherosclerosis, acute coronary syndrome, peripheral vascular disease, restenosis, or vasospasm in a mammal.

In yet other aspects, the compounds of the invention can be used for treating or inhibiting Alzheimer's disease, cognitive decline, senile dementia, or type II diabetes in a mammal.

DETAILED DESCRIPTION OF THE INVENTION

Compounds of the present invention are believed to block interleukin-1β, (IL-1β) induced nuclear factor κB (NF-κB) luciferase reporter activity or interleukin-6 (IL-6) expression in an ER dependent fashion in human endothelial cells. These compounds appear to show no proliferative effects on uterine and breast tissue associated with estrogen in vivo. This lack of estrogen side effects appears to be confirmed in vitro by the lack of expression of creatine kinase (CK), a classic estrogen responsive gene. The selective anti-inflammatory compounds described herein are expected to prove useful for the treatment and prevention of chronic inflammatory diseases without stimulating uterine and breast cell proliferation as found with classic estrogens The compounds of the invention include phenol substituted indazoles. In certain aspects, the invention relates to substituted [(1H-indazol-3-yl)methyl]phenols and the substituted (hydroxyphenyl)(1H-indazol-3-yl)methanones compounds. The invention also relates to use of these compounds as anti-inflammatory agents. The compounds of the invention are useful in the treatment and prevention of diseases that are associated with chronic inflammation.

This invention provides anti-inflammatory compounds of formulas I and II as defined herein.

In some embodiments, the compound is of the formula:

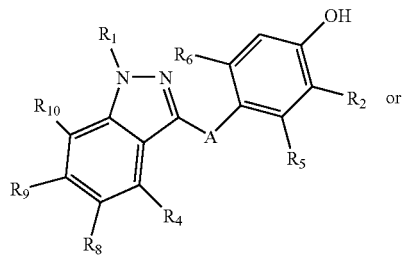

or

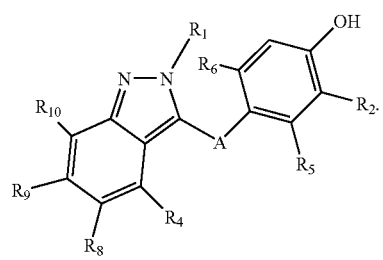

In other embodiments, the compound is of the formula:

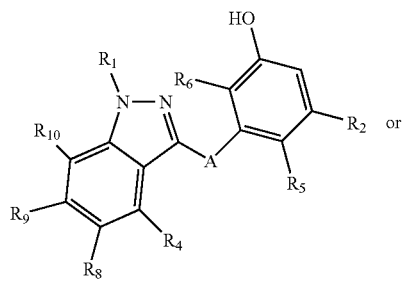

or

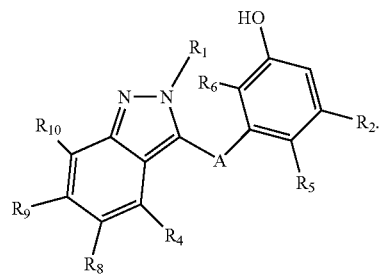

Some compounds of the invention comprise those of formula I (1H-indazoles). Other compound of the invention are of formula II (2H-indazoles).

In certain embodiments, $R_{10}$ is $CF_3$. In other embodiments, $R_1$ is H, lower alkyl, alkenyl, cycloalkyl, aryl or aralkyl where lower means 1-6 carbon atoms. In yet other embodiments, $R_1$ is H, n-propyl, i-propyl, cyclopentyl, benzyl, 3-methoxyphenyl, 2-bromophenyl, 2-methylprop-2-enyl, 2-methylbut-2-enyl, 3-methylbut-2-enyl, or but-2-enyl.

In some embodiments $R_7$ is hydrogen. $R_3$ may be for example hydrogen. In some embodiments A is —(C=O)—, —$CH_2$— or —CHOH—. $R_2$, $R_3$, $R_4$, $R_8$ and $R_9$ may each be for example hydrogen.

Some preferred compounds of this invention, because of their outstanding biological activities include:
3-[(1H-indazol-3-yl)methyl]phenol;
3-[hydroxy(1-propyl-1H-indazol-3-yl)methyl]phenol;
(3-hydroxyphenyl)(1-propyl-1H-indazol-3-yl)methanone;
(1-cyclopentyl-1H-indazol-3-yl)(3-hydroxyphenyl)methanone;
(3-hydroxyphenyl) (1-isopropyl-1H-indazol-3-yl)methanone;
3-[(1-cyclopentyl-1H-indazol-3-yl)methyl]phenol;
(4-hydroxyphenyl)[7-(trifluoromethyl)-1H-indazol-3-yl]methanone;
[1-cyclopentyl-7-(trifluoromethyl)-1H-indazol-3-yl](4-hydroxyphenyl)methanone;
(4-hydroxyphenyl)[1-isopropyl-7-(trifluoromethyl)-1H-indazol-3-yl]methanone;
(3-hydroxyphenyl)[7-(trifluoromethyl)-1H-indazol-3-yl]methanone;
(3-hydroxyphenyl)[1-propyl-7-(trifluoromethyl)-1H-indazol-3-yl]methanone;
[1-cyclopentyl-7-(trifluoromethyl)-1H-indazol-3-yl](3-hydroxyphenyl)methanone;
(3-hydroxyphenyl)[1-isopropyl-7-(trifluoromethyl)-1H-indazol-3-yl]methanone;
(3-hydroxyphenyl)(1-isobutyl-1H-indazol-3-yl)methanone;
(1-allyl-1H-indazol-3-yl)(3-hydroxyphenyl)methanone;
(3-hydroxyphenyl)[1-(2-methylprop-2-enyl)-1H-indazol-3-yl]methanone;
(1-benzyl-1H-indazol-3-yl)(3-hydroxyphenyl)methanone;
(1-cyclohex-2-en-1-yl-1H-indazol-3-yl)(3-hydroxyphenyl)methanone;
(3-hydroxyphenyl)[2-(3-methoxyphenyl)-2H-indazol-3-yl]methanone;
(3-hydroxyphenyl)[1-(3-methoxyphenyl)-1H-indazol-3-yl]methanone; and
[2-(4-bromophenyl)-2H-indazol-3-yl](3-hydroxyphenyl)methanone.

The term "alkyl", employed alone, is defined herein as, unless otherwise stated, either a ($C_1$-$C_{20}$) straight chain or ($C_3$-$C_{20}$) branched-chain monovalent saturated hydrocarbon moiety. Examples of saturated hydrocarbon alkyl moieties include, but are not limited to, chemical groups such as methyl, ethyl, n-propyl, isopropyl, n-butyl, tert-butyl, isobutyl, sec-butyl; higher homologs such as n-pentyl, n-hexyl, n-heptyl, n-octyl, and the like. It is preferred that straight chain alkyl moieties have 1-6 carbon atoms, and branched alkyl moieties have 3-8 carbon atoms.

The term "alkenyl", employed alone, is defined herein as, unless otherwise stated, either a ($C_2$-$C_{20}$) straight chain or ($C_3$-$C_{20}$) branched-chain monovalent hydrocarbon moiety containing at least one double bond. Such hydrocarbon alkenyl moieties may be mono or polyunsaturated, and may exist in the E or Z configurations. The compounds of this invention are meant to include all possible E and Z configurations. Examples of mono or polyunsaturated hydrocarbon alkenyl moieties include, but are not limited to, chemical groups such as vinyl, 2-propenyl, isopropenyl, crotyl, 2-isopentenyl, butadienyl, 2-(butadienyl), 2,4-pentadienyl, 3-(1,4-pentadienyl), and higher homologs, isomers, and the like. It is preferred that straight chain alkenyl moieties have 2-7 carbon atoms, and branched alkenyl moieties have 3-8 carbon atoms.

The term "alkynyl", employed alone, is defined herein as, unless otherwise stated, either a ($C_2$-$C_{20}$) straight chain or ($C_3$-$C_{20}$) branched-chain monovalent hydrocarbon moiety containing at least one triple bond. Examples of alkynyl moieties include, but are not limited to, chemical groups such as ethynyl, 1-propynyl, 1-(2-propynyl), 3-butynyl, and higher homologs, isomers, and the like. It is preferred that straight chain alkynyl moieties have 2-7 carbon atoms, and branched alkynyl moieties have 3-8 carbon atoms.

The term "alkylene", employed alone or in combination with other terms, is defined herein as, unless otherwise stated, either a ($C_1$-$C_{20}$) straight chain or ($C_2$-$C_{20}$) branched-chain bivalent hydrocarbon moiety derived from an alkane; or a ($C_2$-$C_{20}$) straight chain or branched-chain bivalent hydrocarbon moiety derived from an alkene. Such hydrocarbon alkylene moieties may be fully saturated, or mono or polyunsaturated, and may exist in the E or Z configurations. The compounds of this invention are meant to include all possible E and Z configurations. Examples of saturated and unsaturated hydrocarbon alkylene moieties include, but are not limited to, bivalent chemical groups such as —$CH_2$—, —$CH_2CH_2$—, —$CH_2CH_2CH_2$—, —$CH_2CH_2CH_2CH_2$—, —CH=CH—, —CH=CHCH=CH—, vinylidene, and higher homologs, isomers, and the like. Preferred alkylene chains have 2-7 carbon atoms.

The term "cycloalkyl", employed alone or in combination with other terms, is defined herein as, unless otherwise stated, a monocyclic, bicyclic, tricyclic, fused, bridged, or spiro monovalent saturated hydrocarbon moiety of 3-10 carbon atoms, wherein the carbon atoms are located inside or outside of the ring system. Any suitable ring position of the cycloalkyl moiety may be covalently linked to the defined chemical structure. Examples of cycloalkyl moieties include, but are not limited to, chemical groups such as cyclopropyl, cyclopropylmethyl, cyclobutyl, cyclopentyl, cyclohexyl, cyclohexylmethyl, cyclohexylethyl, cycloheptyl, norbornyl, adamantyl, spiro[4.5]decanyl, and homologs, isomers, and the like.

The term "cycloalkenyl", employed alone or in combination with other terms, is defined herein as, unless otherwise stated, a monocyclic, bicyclic, tricyclic, fused, bridged, or spiro monovalent unsaturated hydrocarbon moiety of 3-10 carbon atoms containing at least one double bond, wherein the carbon atoms are located inside or outside of the ring system. Any suitable ring position of the cycloalkenyl moiety may be covalently linked to the defined chemical structure. Examples of cycloalkenyl moieties include, but are not limited to, chemical groups such as cyclopropenyl, cyclopropenylmethyl cyclobutenyl, cyclopentenyl, cyclohexenyl, cyclohexenylmethyl, cyclohexenylethyl, cycloheptenyl, norbornenyl, and homologs, isomers, and the like.

The term "cycloalkylene", employed alone, is defined herein as, unless otherwise stated, a bivalent moiety of 3-10 carbon atoms derived from a monocyclic, bicyclic, tricyclic, fused, bridged, or spiro hydrocarbon. Such hydrocarbon cycloalkylene moieties may be fully saturated, or mono or polyunsaturated, and may exist in the E or Z configurations. The compounds of this invention are meant to include all possible E and Z configurations. Any suitable ring position of the cycloalkylene moiety may be covalently linked to the defined chemical structure. Examples of saturated and unsaturated hydrocarbon cycloalkylene moieties include, but are not limited to, bivalent chemical groups such as cyclopropylene, cyclopentylene, cyclohexylene, cyclohexenylene, trans-decahydronaphthalenylene, spiro[3.3]heptenylene, and higher homologs, isomers, and the like.

The terms "halo" or "halogen", employed alone or in combination with other terms, is defined herein as, unless otherwise stated, a fluorine, chlorine, bromine, or iodine atom.

The term "monofluoroalkyl", employed alone, is defined herein as, unless otherwise stated, either a ($C_1$-$C_{10}$) straight chain or ($C_3$-$C_{10}$) branched-chain monovalent saturated hydrocarbon moiety containing only one fluorine atom.

Examples of monofluoroalkyl moieties include, but are not limited to, chemical groups such as —CH$_2$F, —CH$_2$CH$_2$F, —CH(CH$_3$)CH$_2$CH$_2$F, and higher homologs, isomers, and the like. Preferred chain lengths are from 1-6 carbon atoms for straight chains and from 3-8 carbon atoms for branched chains.

The term "monofluoroalkenyl", employed alone, is defined herein as, unless otherwise stated, either a (C$_2$-C$_{10}$) straight chain or (C$_3$-C$_{10}$) branched-chain monovalent unsaturated hydrocarbon moiety, containing only one fluorine atom and at least one double bond. Examples of monofluoroalkenyl moieties include, but are not limited to, chemical groups such as —CH═CH$_2$F, —CH$_2$CH═CH$_2$F, —CH═CHCH$_2$F, —C(CH$_3$)═CHF and higher homologs, isomers, and the like. Preferred chain lengths are from 2-7 carbon atoms for straight chains and from 3-8 carbon atoms for branched chains.

The term "perfluoroalkyl", employed alone or in combination with other terms, is defined herein as, unless otherwise stated, either a (C$_1$-C$_{10}$) straight chain or (C$_3$-C$_{10}$) branched-chain monovalent saturated hydrocarbon moiety containing two or more fluorine atoms. Examples of perfluoroalkyl moieties include, but are not limited to, chemical groups such as trifluoromethyl, —CH$_2$CF$_3$, —CF$_2$CF$_3$, and —CH(CF$_3$)$_2$, and homologs, isomers, and the like. Preferred chain lengths are from 1-7 carbon atoms for straight chains and from 3-8 carbon atoms for branched chains.

The term "aryl", employed alone or in combination with other terms, is defined herein as, unless otherwise stated, an aromatic carbocyclic moiety of up to 20 carbon atoms, e.g., 6-20 carbon atoms, which may be a single ring (monocyclic) or multiple rings (bicyclic, up to three rings) fused together or linked covalently. Any suitable ring position of the aryl moiety may be covalently linked to the defined chemical structure. Examples of aryl moieties include, but are not limited to, chemical groups such as phenyl, 1-naphthyl, 2-naphthyl, dihydronaphthyl, tetrahydronaphthyl, biphenyl. anthryl, phenanthryl, fluorenyl, indanyl, biphenylenyl, acenaphthenyl, acenaphthylenyl, and the like. It is preferred that the aryl moiety contain 6-14 carbon atoms.

The terms "arylalkyl" or "aralkyl", employed alone or in combination with other terms, are defined herein as, unless otherwise stated, an aryl group, as herein before defined, suitably substituted on any open ring position with an alkyl moiety wherein the alkyl chain is either a (C$_1$-C$_6$) straight or (C$_2$-C$_7$) branched-chain saturated hydrocarbon moiety. Examples of arylalkyl moieties include, but are not limited to, chemical groups such as benzyl, 1-phenylethyl, 2-phenylethyl, diphenylmethyl, 3-phenylpropyl, 2-phenylpropyl, fluorenylmethyl, and homologs, isomers, and the like.

The term "heteroaryl", employed alone or in combination with other terms, is defined herein as, unless otherwise stated, an aromatic heterocyclic ring system, which may be a single ring (monocyclic) or multiple rings (bicyclic, up to three rings) fused together or linked covalently and having for example 5 to 20 ring members. The rings may contain from one to four hetero atoms selected from nitrogen (N), oxygen (O), or sulfur (S), wherein the nitrogen or sulfur atom(s) are optionally oxidized, or the nitrogen atom(s) are optionally substituted (e.g., by alkyl such as methyl) or quarternized. Any suitable ring position of the heteroaryl moiety may be covalently linked to the defined chemical structure. Examples of heteroaryl moieties include, but are not limited to, heterocycles such as furan, thiophene, pyrrole, N-methylpyrrole, pyrazole, N-methylpyrazole, imidazole, N-methylimidazole, oxazole, isoxazole, thiazole, isothiazole, 1H-tetrazole, 1-methyltetrazole, 1,3,4-oxadiazole, 1H-1,2,4-triazole, 1-methyl-1,2,4-triazole, 1,3,4-triazole, 1-methyl-1,3,4-triazole, pyridine, pyrimidine, pyrazine, pyridazine, benzoxazole, benzisoxazole, benzothiazole, benzofuran, benzothiophene, thianthrene, dibenzo[b,d]furan, dibenzo[b,d]thiophene, benzimidazole, N-methylbenzimidazole, indole, indazole, quinoline, isoquinoline, quinazoline, quinoxaline, purine, pteridine, 9H-carbazole, β-carboline, and the like.

The term "heteroarylalkyl", employed alone or in combination with other terms, is defined herein as, unless otherwise stated, a heteroaryl group, as herein defined, suitably substituted on any open ring position with an alkyl moiety, wherein the alkyl chain is either a (C$_1$-C$_6$) straight or (C$_2$-C$_7$) branched-chain saturated hydrocarbon moiety. Examples of heteroarylalkyl moieties include, but are not limited to, chemical roups such as furanylmethyl, thienylethyl, indolylmethyl, and the like.

Heteroaryl chemical groups, as herein before defined, also include saturated or partially saturated heterocyclic rings, e.g. saturated or partially saturated heterocyclyl groups of 4-20 ring members. Examples of saturated or partially saturated heteroaryl moieties include, but are not limited to, heterocyclyl groups such as azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothienyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dihydro-1,4-dioxanyl, tetrahydrofuranyl, tetrahydrothienyl, tetrahydroquinolinyl, tetrahydroisoquinolinyl, and the like.

The term "acyl", employed alone or in combination with other terms, is defined herein as, unless otherwise stated, either an alkyl, arylalkyl, heteroarylalkyl, in which the alkyl or alkyl part is a (C$_2$-C$_{10}$) straight chain, or (C$_4$-C$_{11}$) branched-chain monovalent hydrocarbon moiety; wherein the carbon atom, covalently linked to the defined chemical structure, is oxidized to the carbonyl oxidation state. Such hydrocarbon moieties may be mono or polyunsaturated, and may exist in the E or Z configurations. The compounds of this invention are meant to include all possible E and Z configurations. Examples of acyl moieties include, but are not limited to, chemical groups such as acetyl, propionyl, butyryl, 3,3-dimethylbutyryl, trifluoroacetyl, pivaloyl, hexanoyl, hexenoyl, decanoyl, benzoyl, nicotinyl, isonicotinyl, and homologs, isomers, and the like.

The term "hydroxyalkyl", employed alone or in combination with other terms, is defined herein as, unless otherwise stated, a (C$_1$-C$_{10}$) straight chain hydrocarbon, substituted with a hydroxyl group. In some embodiments, the hydroxyl group is terminally substituted. Examples of hydroxyalkyl moieties include chemical groups such as —CH$_2$OH, —CH$_2$CH$_2$OH, —CH$_2$CH$_2$CH$_2$OH, and higher homologs.

The term "alkoxy", employed alone or in combination with other terms, is defined herein as, unless otherwise stated, either a (C$_1$-C$_{10}$) straight chain or (C$_3$-C$_{10}$) branched-chain hydrocarbon covalently bonded to an oxygen atom. Examples of alkoxy moieties include, but are not limited to, chemical groups such as methoxy, ethoxy, isopropoxy, sec-butoxy, tert-butoxy, decanoxy, and homologs, isomers, and the like.

The terms "aryloxy" or "heteroaryloxy", employed alone or in combination with other terms, or unless otherwise stated, are aryl or heteroaryl groups, as herein before defined, which are further covalently bonded to an oxygen atom.

Examples of aryloxy or heteroaryloxy moieties include, but are not limited to, chemical groups such as $C_6H_5O$—, 4-pyridyl-O—, and homologs, isomers, and the like.

The term "carbonyl", employed alone or in combination with other terms, is defined herein as, unless otherwise stated, a bivalent one-carbon moiety further bonded to an oxygen atom with a double bond. An example is

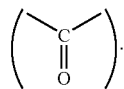

The term "alkoxycarbonyl", employed alone or in combination with other terms, is defined herein as, unless otherwise stated, an alkoxy group, as herein before defined, which is further bonded to a carbonyl group to form an ester moiety. Examples of alkoxycarbonyl moieties include, but are not limited to, chemical groups such as methoxycarbonyl, ethoxycarbonyl, isopropoxycarbonyl, sec-butoxycarbonyl, tert-butoxycarbonyl, decanoxycarbonyl, and homologs, isomers, and the like.

The term "alkylthio", employed alone or in combination with other terms, is defined herein as, unless otherwise stated, either a ($C_1$-$C_{10}$) straight chain or ($C_3$-$C_{10}$) branched-chain hydrocarbon moiety covalently bonded to a sulfur atom. Examples of alkylthio moieties include, but are not limited to, chemical groups such as methylthio, ethylthio, isopropylthio, sec-butylthio, tert-butylthio, decanylthio, and homologs, isomers, and the like. It is preferred that straight chain alkylthio moieties have 1-6 carbon atoms, and branched alkylthio moieties have 3-8 carbon atoms.

The terms "arylthio" or "heteroarylthio", employed alone or in combination with other terms, or unless otherwise stated, are aryl or heteroaryl groups, as herein before defined, which are further covalently bonded to a sulfur atom. Examples of arylthio or heteroarylthio moieties include, but are not limited to, chemical groups such as $C_6H_5S$—, 4-pyridyl-S—, and homologs, isomers, and the like.

The terms "alkoxyalkyl" or "alkylthioalkyl", employed alone or in combination with other terms, are an alkoxy or alkylthio group, as herein before defined, which is further covalently bonded to an unsubstituted ($C_1$-$C_{10}$) straight chain or unsubstituted ($C_2$-$C_{10}$) branched-chain hydrocarbon. Examples of alkoxyalkyl or alkylthioalkyl moieties include, but are not limited to, chemical groups such as, methoxymethyl, methylthioethyl, ethylthioethyl, isopropylthiomethyl, sec-butylthioethyl, —$CH_2CH(CH_3)OCH_2CH_3$, and homologs, isomers, and the like. It is preferred that straight chain alkoxyalkyl or alkylthioalkyl moieties have 1-6 carbon atoms, and branched alkoxyalkyl or alkylthioalkyl moieties have 3-8 carbon atoms.

The terms "aryloxyalkyl", "heteroaryloxyalkyl", "arylthioalkyl", or "heteroarylthioalkyl", employed alone or in combination with other terms, or unless otherwise stated, are aryloxy, heteroaryloxy, arylthio, or heteroarylthio groups, as herein before defined, which are further covalently bonded to an unsubstituted ($C_1$-$C_{10}$) straight chain or unsubstituted ($C_2$-$C_{10}$) branched-chain hydrocarbon. Examples of aryloxyalkyl, heteroaryloxyalkyl, arylthioalkyl, or heteroarylthioalkyl moieties include, but are not limited to, chemical groups such as $C_6H_5OCH_2$—, $C_6H_5OCH(CH_3)$—, 4-pyridyl-O—$CH_2CH_2$—, $C_6H_5SCH_2$—, $C_6H_5SCH(CH_3)$—, 4-pyridyl-S—$CH_2CH_2$—, and homologs, isomers, and the like. It is preferred that straight chain aryloxyalkyl, heteroaryloxyalkyl, arylthioalkyl, or heteroarylthioalkyl moieties have 1-6 carbon atoms, and branched aryloxyalkyl, heteroaryloxyalkyl, arylthioalkyl, or heteroarylthioalkyl moieties have 3-8 carbon atoms.

The term "alkylamino", employed alone or in combination with other terms, or unless otherwise stated, is a moiety with one alkyl group, wherein the alkyl group is an unsubstitued ($C_1$-$C_6$) straight or ($C_3$-$C_6$) branched chain hereunto before defined alkyl group or an unsubstitued ($C_3$-$C_8$) hereunto before defined cycloalkyl group. Examples of alkylamino moieties include, but are not limited to, chemical groups such as —$NH(CH_3)$, —$NH(CH_2CH_3)$, —NH-cyclopentyl, and homologs, and the like.

The term "dialkylamino", employed alone or in combination with other terms, or unless otherwise stated, is a moiety with two independent alkyl groups, wherein the alkyl groups are unsubstitued ($C_1$-$C_6$) straight or ($C_3$-$C_6$) branched chain hereunto before defined alkyl groups or unsubstitued ($C_3$-$C_8$) hereunto before defined cycloalkyl groups. Two groups may be linked to form an unsubstituted ($C_2$-$C_6$)-alkylene- group. Examples of dialkylamino moieties include, but are not limited to, chemical groups such as —$N(CH_3)_2$, —$N(CH_2CH_3)_2$, —$NCH_3(CH_2CH_3)$,

and homologs, and the like.

The term "alkylaminoalkyl" employed alone or in combination with other terms, or unless otherwise stated, is an alkylamino moiety, as herein before defined, which is further covalently bonded to a straight chain alkyl group of 1-6 carbon atoms. Examples of alkylaminoalkyl moieties include, but are not limited to, chemical groups such as —$CH_2NH(CH_3)$, —$CH_2CH_2NH(CH_2CH_3)$, —$CH_2CH_2CH_2NH(CH_2CH_3)$, and homologs, and the like.

The term "dialkylaminoalkyl" employed alone or in combination with other terms, or unless otherwise stated, is a dialkylamino moiety, as herein before defined, which is further covalently bonded to a straight chain alkyl group of 1-6 carbon atoms. Examples of dialkylaminoalkyl moieties include, but are not limited to, chemical groups such as —$CH_2N(CH_3)_2$, —$CH_2CH_2N(CH_2CH_3)_2$, —$CH_2CH_2CH_2NCH_3(CH_2CH_3)$, and homologs, and the like.

The terms "alkylaminocarbonyl" or "dialkylaminocarbonyl", employed alone, or unless otherwise stated, are alkylamino or dialkylamino moieties, as herein before defined, which are further bonded to a carbonyl group. Examples of alkylaminocarbonyl or dialkylaminocarbonyl moieties include, but are not limited to, chemical groups such as —$C(O)NH(CH_3)$, —$C(O)N(CH_2CH_3)_2$, —$C(O)NCH_3(CH_2CH_3)$, and homologs, and the like.

Each of the above terms (e.g., alkyl, aryl, heteroaryl) includes unsubstituted, monosubstituted, and polysubstituted forms of the indicated radical or moiety. Substituents for each type of moiety are provided below.

Substituents for alkyl, alkenyl, alkynyl, cycloalkyl, cycloalkenyl, alkylene, cycloalkylene, the alkyl portion of arylalkyl and heteroarylalkyl, saturated or partially saturated heterocyclic rings, and acyl or carbonyl moieties are, employed alone or in combination with other terms, selected from the group consisting of —R', OR', =O, =NR', =N—OR', —NR'R", —SR', halo, trifluoromethyl, trifluoromethoxy, —OC(O)R', —$CO_2$R', —C(O)NR'R", —OC(O)

NR'R", —NR"C(O)R', —NR"CO$_2$R', —NR'C(O)NR'R", —NH—C(NH$_2$)=NH, —NR'C(NH$_2$)=NH, —NH—C (NH$_2$)=NR', —S(O)R', —S(O)$_2$R', —S(O)$_2$NR'R", cyano, and nitro; wherein, R' or R" are each, independently, hydrogen, unsubstituted (C$_1$-C$_6$)alkyl, unsubstituted (C$_3$-C$_7$)cycloalkyl, aryl, aryl-(C$_1$-C$_3$)alkyl, aryloxy-(C$_1$-C$_3$)alkyl, arylthio-(C$_1$-C$_3$)alkyl, heteroaryl, heteroaryl-(C$_1$-C$_3$)alkyl, heteroaryloxy-(C$_1$-C$_3$)alkyl, or heteroarylthio-(C$_1$-C$_3$)alkyl groups; or if optionally taken together may be linked as an -alkylene- group to form a ring.

The aryl or heteroaryl moieties, employed alone or in combination with other terms, may be optionally mono-, di- or tri-substituted with substituents selected from the group consisting of —R', —OR', —SR', —C(O)R', —CO$_2$R', -alkoxyalkyl, alkoxyalkyloxy, cyano, halogen, nitro, trifluoromethyl, trifluoromethoxy, —NR'R", alkylaminoalkyl, dialkylaminoalkyl, hydroxyalkyl, —S(O)R', —S(O)$_2$R', —SO$_3$R', —S(O)$_2$NR'R", —CO$_2$R', —C(O)NR'R", —OC(O)NR'R", —NR"C(O)R', —NR"CO$_2$R', —NR'C(O)NR'R", —NH—C(NH$_2$)=NH, —NR'C(NH$_2$)=NH, —NH—C(NH$_2$)=NR', —S(O)R', and —S(O)$_2$R'; wherein, R' or R" are each, independently, hydrogen, (C$_1$-C$_6$)alkyl, (C$_3$-C$_7$)cycloalkyl, aryl, aryl-(C$_1$-C$_3$)alkyl, aryloxy-(C$_1$-C$_3$)alkyl, arylthio-(C$_1$-C$_3$) alkyl, heteroaryl, heteroaryl-(C$_1$-C$_3$)alkyl, heteroaryloxy-(C$_1$-C$_3$)alkyl, or heteroarylthio-(C$_1$-C$_3$)alkyl groups; or if optionally taken together may be linked as an -alkylene- group to form a ring.

A pro-drug is defined as a compound which is convertible by in vivo enzymatic or non-enzymatic metabolism (e.g. hydrolysis) to a compound of Formula (I) or Formula (II).

The compounds of the present invention may contain an asymmetric atom, and some of the compounds may contain one or more asymmetric atoms or centers, which may thus give rise to optical isomers (enantiomers) and diastereomers. While shown without respect to the stereochemistry in Formula (I) or (II), the present invention includes such optical isomers (enantiomers) and diastereomers (geometric isomers); as well as the racemic and resolved, enantiomerically pure R and S stereoisomers; as well as other mixtures of the R and S stereoisomers and pharmaceutically acceptable salts thereof. Optical isomers may be obtained in pure form by standard procedures known to those skilled in the art, and include, but are not limited to, diasteromeric salt formation, kinetic resolution, and asymmetric synthesis. It is also understood that this invention encompasses all possible regioisomers, and mixtures thereof, which may be obtained in pure form by standard separation procedures known to those skilled in the art, and include, but are not limited to, column chromatography, thin-layer chromatography, and high-performance liquid chromatography.

The compounds of the present invention may contain isotopes of atoms for diagnostic, therapeutic, or metabolic purposes. Such isotopes may or may not be radioactive.

The compounds of this invention include racemates, enantiomers, geometric isomers, or pro-drugs of the compounds shown herein.

Pharmaceutically acceptable salts of the compounds of compounds of the instant mention with an acidic moiety can be formed from organic and inorganic bases. Suitable salts with bases are, for example, metal salts, such as alkali metal or alkaline earth metal salts, for example sodium, potassium, or magnesium salts; or salts with ammonia or an organic amine, such as morpholine, thiomorpholine, piperidine, pyrrolidine, a mono-, di- or tri-lower alkylamine, for example ethyl-tert-butyl-, diethyl-, diisopropyl-, triethyl-, tributyl- or dimethylpropylamine, or a mono-, di-, or trihydroxy lower alkylamine, for example mono-, di- or triethanolamine. Internal salts may furthermore be formed. Similarly, when a compound of the present invention contains a basic moiety, salts can be formed from organic and inorganic acids. For example salts can be formed from acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known pharmaceutically acceptable acids.

As used in accordance with this invention, the term "providing," with respect to providing a compound or substance covered by this invention, means either directly administering such a compound or substance, or administering a pro-drug, derivative, or analog which will form the effective amount of the compound or substance within the body. This invention also covers providing the compounds of this invention to treat the disease states disclosed herein that the compounds are useful for treating.

Solvates (e.g., hydrates) of the compounds of the present invention are also within the scope of the present invention. Methods of solvation are generally known in the art. Accordingly, the compounds of the instant invention can be in the free or hydrate form, and can be obtained by methods exemplified by the following schemes below.

Process of the Invention

Compounds of formula I, where A is defined as C=O and R$_1$=alkyl, can be prepared by as shown in Scheme 1.

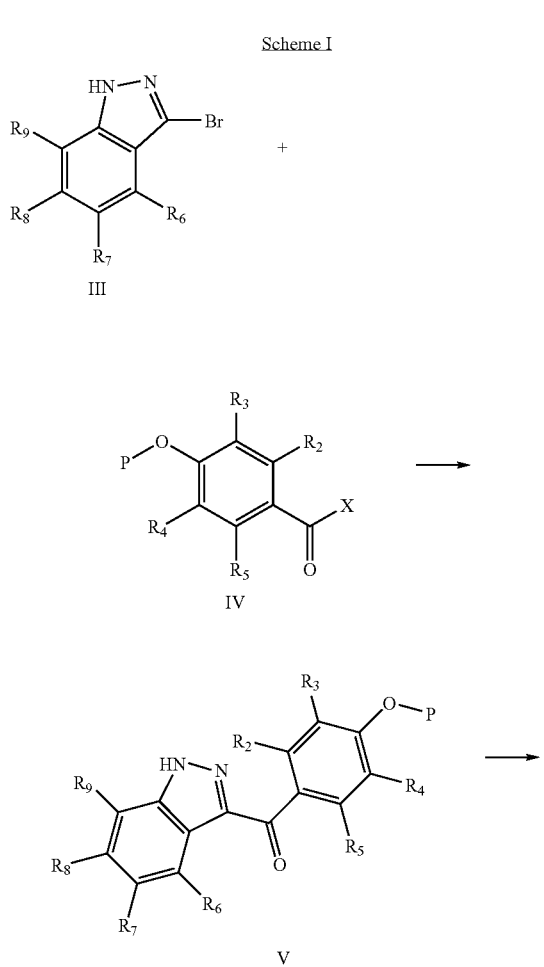

Scheme I

-continued

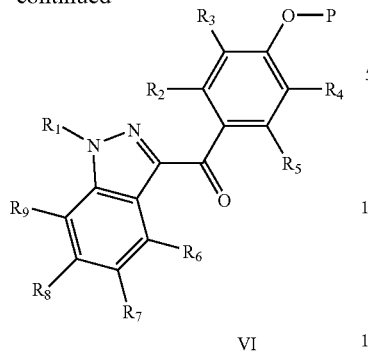

VI wherein

P is a phenol protecting group, preferably benzyl, methyl or t-butyldiphenylsilyl;

X is Cl or —N(CH$_3$)OCH$_3$; and

R$_2$, R$_3$, R$_4$, R$_5$, R$_6$, R$_7$, R$_8$, and R$_9$ are defined as above and chosen to be compatible with the reaction scheme.

According to the procedure described by W. M. Welch et al., Synthesis 1992, 937, the dianion of III is generated in a suitable solvent such as diethyl ether (Et$_2$O) at −78° C. by the dropwise addition of 1 equivalent of n-butyllithium followed by 2 equivalents of t-butyl lithium. The acid chloride (or Weinreb amide prepared as described by Nahm, S.; Weinreb, S. M., *Tetrahedron Lett.* 1981, 22(39), 3815) IV is added as to the cooled solution and the solution is allowed to warm to ambient temperature. The intermediates of formula V are isolated via chromatography over silica gel as known to those skilled in the art.

Compounds of formula VI are prepared by treatment of the intermediate V with sodium hydride in a suitable solvent such as dimethylformamide (DMF). When gas evolution ceases an alkyl halide is added and the solution is stirred at ambient temperature preferably overnight. The products VI are isolated by either chromatography or recrystallization from a suitable solvent known to those skilled in the art.

Compounds of formula VI where R1 is aryl are prepared by reaction under anhydrous conditions of V with an appropriately substituted phenyl boronic acid in a suitable solvent such as methylene chloride in the presence of a suitable base such as pyridine in the presence of a catalyst like anhydrous copper (II) acetate over powdered 4 Angstrom molecular sieves.

Compounds of formula I are prepared from VI via a deprotection step. When P=benzyl, deprotection to the phenol is accomplished by hydrogenation over 10% palladium on carbon using either hydrogen gas, or catalytic hydride transfer with cyclohexene or ammonium formate When P is methyl, deprotection may be carried out using BBr$_3$ with cyclohexene as a scavenger for HBr.

When P is t-butyldiphenylsilyl, deprotection can be accomplished with tetrabutylammonium fluoride (TBAF).

Compounds of formula II are prepared in an analogous fashion to the regioisomers of formula I as outlined in Scheme 2

Scheme 2

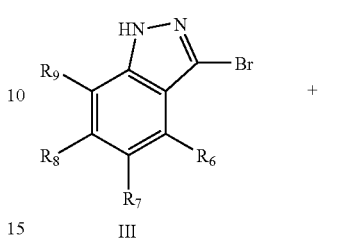

III

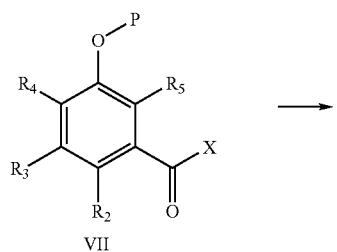

VII

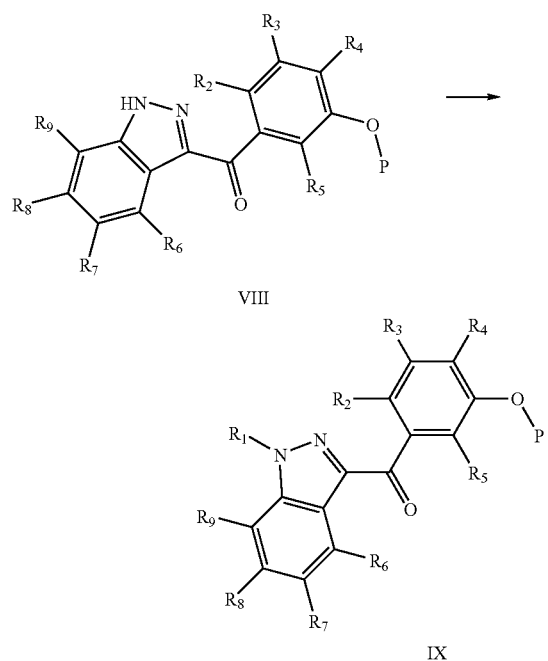

VIII

IX

Intermediates of formula VIII are prepared by the reaction of compounds of formula III with compounds of formula VII as previously described. Compounds of formula IX are prepared by the regiospecific alkylation described previously for the regioisomer VI followed by an appropriate deprotection step to give the final compound of formula II.

Compounds of formula V may also be prepared by the reaction of compounds of formula X with compounds of formula XI in a suitable solvent such as tetrahydrofuran (THF) as outlined in Scheme 3.

Scheme 3

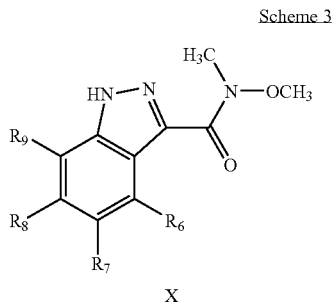

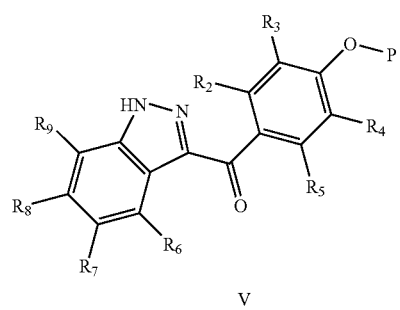

Compounds of formula VIII can also be prepared in an analogous fashion to the regioisomer V from the reaction of compounds of formula X with compounds of formula XII as outlined in Scheme 4

Scheme 4

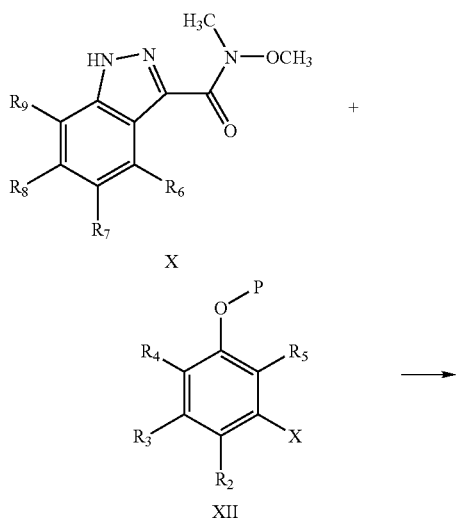

-continued

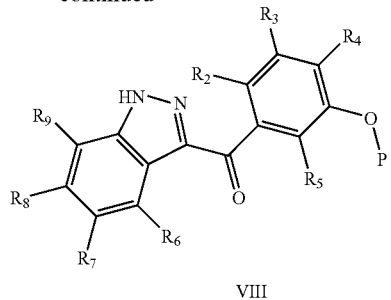

When X is MgBr, the reaction is typically heated at 50° C. as a solution in tetrahydrofuran (THF) for a period from 1 to 24 hours.

When X is Br, the reagents are typically combined in THF and cooled to −78° C. and 1.2 equivalents of n-butyllithium (typically 1.6 molar in hexane) is added dropwise and stirred at −78° C. till the reaction is complete.

An alternate preparation of compounds of formula V is outlined in Scheme 5.

Scheme 5

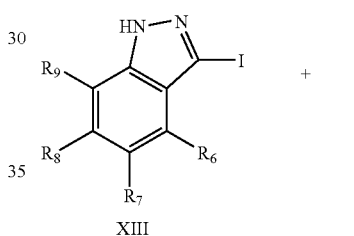

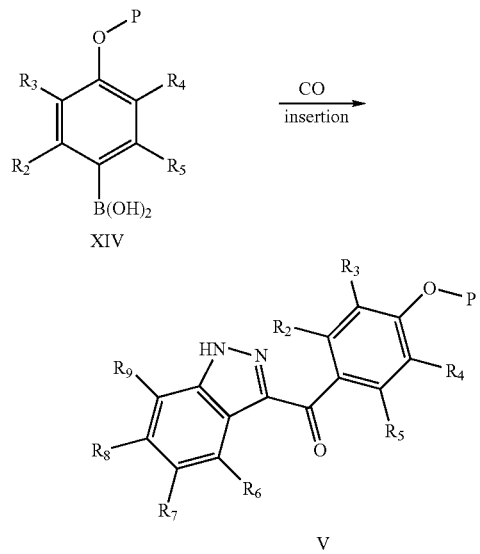

Using biaryl carbonylative cross-coupling conditions described By T. Ishiyama, H. Kizaki, T. Hayashi, A. Suzuki, N. Miyaura, *J. Org. Chem.*, 1998, 63, 4726 the biaryl ketone V can be prepared by the reaction of XIII with the boronic acid XIV in a suitable solvent such as anisole using 3 mol % palladium dichloride bis triphenylphosphine and 4 equivalents of potassium carbonate and under an atmosphere of carbon monoxide. The mixture is heated at 80° C. overnight and then purified by flash chromatography known to those skilled in the art.

Using the same conditions for biaryl carbonylative cross-coupling, compounds of formula VIII can be prepared as outlined in Scheme 6.

Scheme 6

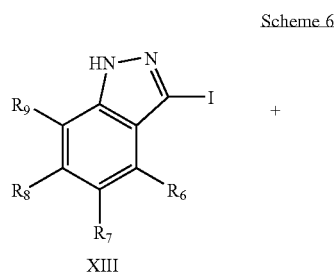

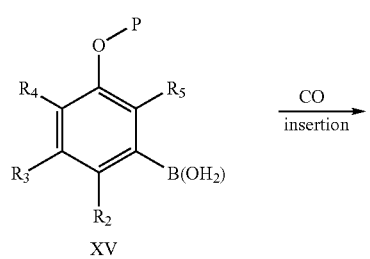

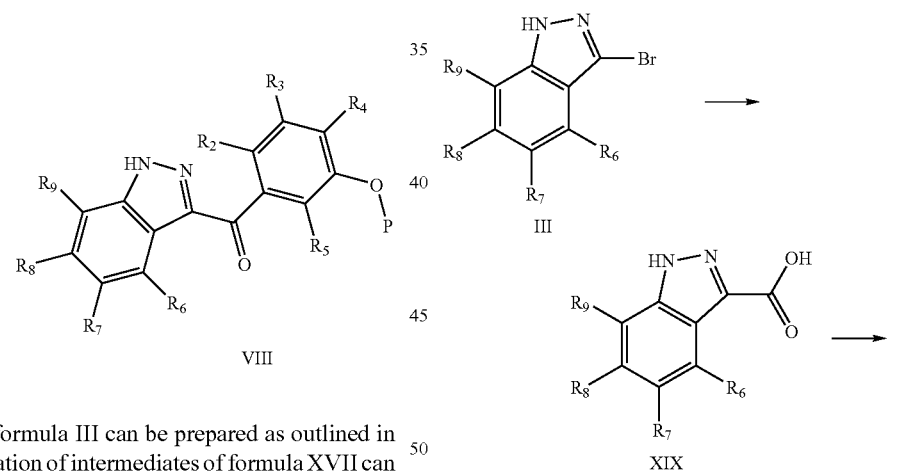

Compounds of formula III can be prepared as outlined in Scheme 7. Bromination of intermediates of formula XVII can be accomplished by the method described by B. E. Boulton, B. A. Coller, *Aust. J. Chem.*, 1974, 27, 2343 or by other methods known to those skilled in the art.

Scheme 7

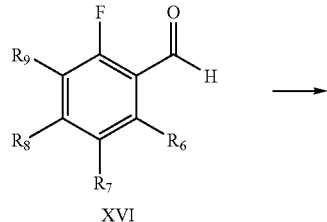

-continued

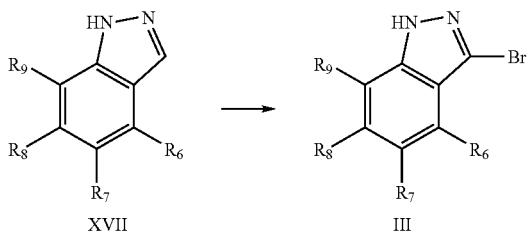

The intermediates of compound XVII are either commercially available or can be prepared from the reaction of substituted 2-fluoro-benzaldehydes of formula XVI, either commercially available or readily prepared by general methods known to those skilled in the art, with an excess of hydrazine hydrate and DMAP in pyridine at 100° C. overnight.

Compounds of formula X can be readily prepared as shown in Scheme 8 by the reaction of compounds of formula III with copper cyanide in an appropriate solvent such as N-methylpyrrolidinone followed by hydrolysis under acidic conditions to compounds of formula XIX. The Weinreb amides of formula X are then generated by the reaction of the carboxylic acid with N,O-dimethylhydroxylamine and N,N-carbonyldiimidazole in a suitable solvent such as DMF as described by Robertson, *J. Med. Chem.*, 1990, 23, 3176.

Scheme 8

Compounds of formula XIII can be readily prepared from compounds of formula XVII using the procedure described by V. Collot, P Bovy, S. Rault, *Tetrahedron Letters*, 2000, 41, 9053 as outlined in Scheme 9.

Scheme 9

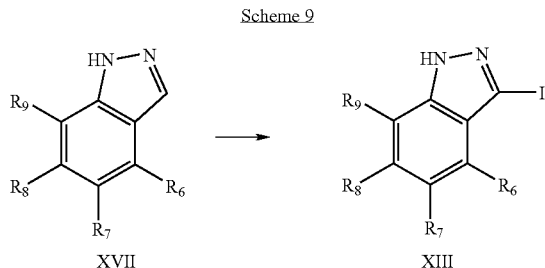

Also according to the present invention there is provided a method of treating atherosclerosis, myocardial infarction, congestive heart failure, arthritis and inflammatory bowel disease in humans or other mammals which comprises administering to a human or other mammal an anti-inflammatory effective amount of a compound of the present invention.

It is understood that the effective dosage of the active compounds of this invention may vary depending upon the particular compound utilized, the mode of administration, the condition, and severity thereof, of the condition being treated, as well as the various physical factors related to the individual being treated. For treating atherosclerosis, myocardial infarction, congestive heart failure, arthritis and/or inflammatory bowel disease, generally satisfactory results may be obtained when the compounds of this invention are administered to the individual in need at a daily dosage of from about 0.1 mg to about 1 mg per kilogram of body weight, preferably administered in divided doses two to six times per day, or in a sustained release form. For most large mammals, the total daily dosage is from about 3.5 mg to about 140 mg, preferably from about 3.5 to about 5 mg. In the case of a 70 kg human adult, the total daily dose will generally be from about 7 mg to about 70 mg and may be adjusted to provide the optimal therapeutic result.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elexir may contain, in addition to the active ingredients, sucrose as a sweetening agent, methyl and propyl parabens as preservatives, a dye and a flavoring such as cherry or orange flavor.

These active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, the preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Also according to the present invention there are provided processes for producing the compounds of the present invention.

In Vitro Methods

Cells

T-175 flasks of 100% confluent HAECT-1 cells (immortalized human aortic endothelial cells) were washed with 8 ml of HBSS (HEPES buffered saline solution) and infected for four hours with 6 ml of a 1:10 dilution of Ad5-wt-hERα virus (an adenovirus transfection vector that mediates CMV promoter driven expression of human ERα) in phenol red free Endothelial Cell Basal medium (Clonetics, San Diego Calif., Catalog # CC-3129) containing 0.25% bovine serum albumin (EBM-BSA). After four hours, cells were washed with EBM-BSA and incubated overnight in the same medium. Following overnight incubation, cells were washed with EBM-BSA and infected for 2 hours with 6 ml of a 1:10 dilution of Ad5-3× (NFκB).Luc virus (Adenovirus luciferase expression vector driven by 3 repeats of the MHC NFκb site 5' to the thymidine kinase promoter) in EBM-BSA. After two hours, cells were washed and incubated at 34° C. for 1 hour. Cells were then washed, trypsinized, counted and resuspended in 95% FBS/5% dimethylsulfoxide at a concentration of $4 \times 10^6$ cells/ml, frozen as 1 or 5 ml aliquots in cryo-vials and stored at −150° C. Control (no ER infection) cells were processed as above without Ad5-wt-hERα virus infection.

IL-6 and Creatine Kinase Assays

ERα infected HAECT-1 cells or control cells were thawed, diluted 42× in warm EBM-BSA, plated into 96-well plates at 0.1 ml/well and incubated for 4 h at 34° C. Test compounds were added to the cells as 2× stocks in EBM-BSA containing 2 ng/ml IL-1β (R&D Systems) and plates were returned to the incubator (34° C.). After 15-20 h, 100 μl aliquots of media were removed from the cells and assayed for IL-6 content using a BioSource human IL-6 ELISA Kit. Cells were subsequently washed with 300 μl of Dulbecco's phosphate buffered saline and lysed in 50 μl of Cell Culture Lysis Reagent (Promega). Luciferase was determined on a Wallac Victor$^2$ Luminometer (Gaithersburg, Md.) using 10 μl of lysate and mixing with 100 μl of Promega Luciferase Assay reagent. Creatine kinase was determined from the rate of increase in $A_{340}$ following addition of 100 μl of CK assay reagent (Sigma, cat. No 47-10) to the remainder of the cell lysate.

Data Analyses

For $IC_{50}$ and $EC_{50}$ calculations, mean IL-6, luciferase or CK values versus $\log_{10}$ of the compound concentration were fitted to a four parameter logistic equation. The $IC_{50}/EC_{50}$ value, 'Hill slope', upper and lower limits of the curve were iteratively estimated.

Mice

Ovariectomized C57BL/6 mice (16-20 g) (Taconic) were separated into groups of 8. After 5-7 days of recuperation, the mice were fed a chow diet or an atherogenic diet (15.75% fat, 1.25% cholesterol and 0.5% sodium cholate) (Purina diet #21539). EE or test compound was administered once daily by gavage in a methylcellulose/tween vehicle (0.1 ml per mouse) for 5 weeks. At the end of the experimental period, the liver was collected and uterine wet weight was recorded.

RNA Analysis

Liver total RNA was prepared by using Trizol reagent (BRL). Estrogen and compound regulation of NF-κB target genes were verified by real time RT-PCR using an ABI PRISM 7700 Sequence Detection System according to the manufacturer's protocol (Applied Biosystems). The data was analyzed using the Sequence Detector v1.7 software (Applied Biosystems) and normalized to GAPDH using the Applied Biosystems primer set.

In Vitro Results

Table 1 summarizes the activities of compounds contained herein in the HAECT-1 NF-κB, IL-6 and creatine kinase assays in Ad5-wt-ER infected cells and is compared to activities of the same compounds in the HAECT-1 NF-κB and creatine kinase assays in uninfected cells.

TABLE 1

Effects of 17-β-estradiol on NF-κB, IL-6 and CK expression in Ad5-wt-ER infected HAECT-1 cells

| I. Example # | ER/NF-KB-luc | | ER/IL-6 | | ER/CK | |
|---|---|---|---|---|---|---|
| | $IC_{50}$ (nM) | % Eff* | $IC_{50}$ (nM) | % Eff | $EC_{50}$ (nM) | % Eff* |
| E2 | 1 | 100 | 1.7 | 100 | 5.8 | 100 |
| 3 | 722 | 70 | | | 2636 | 35 |
| 4 | 170 | 77 | 66 | 109 | 1330 | 57 |
| 5 | 1072 | 83 | | | 1788 | 55 |
| 6 | 570 | 54 | | | ia | |
| 7 | 1005 | 43 | | | ia | |
| 8 | 94 | 87 | | | ia | |
| 9 | 107 | 80 | | | ia | |
| 10 | 593 | 88 | | | ia | |
| 11 | 198 | 82 | | | ia | |
| 12 | 54 | 73 | | | 139 | 32 |
| 13 | 63 | 85 | | | ia | |
| 14 | 388 | 103 | | | ia | |
| 17 | 710 | 100 | | | 1572 | 51 |
| 18 | 1235 | 92 | | | ia | |
| 19 | 409 | 92 | | | ia | |
| 20 | 155 | 87 | | | ia | |
| 22 | 475 | 75 | | | ia | |
| 23 | 82 | 79 | | | ia | |

*Efficacy values are relative to the maximal inhibition (NF-κB or IL-6 assay) or stimulation (CK assay) observed with E2

E2 inhibits NF-κB and IL-6 expression in Ad5-wt-ER infected HAECT-1 cells with an $IC_{50}$ value around 1 nM and induces expression of creatine kinase in the same cells with similar potency (5.8 nM). In contrast, compounds of the present invention potently and efficaciously inhibit NF-κB and IL-6 expression in Ad5-wt-ER infected HAECT-1 cells but do not induce CK expression (Table 1) in an ER-dependent manner. The ability of compounds of the present invention to inhibit NF-κB and IL-6 expression without inducing CK activity (Table 1) is consistent with an anti-inflammatory activity in the absence of classic estrogenic activity.

In Vivo Activity

To determine the ability of estrogens to regulate the development of diet-induced inflammation in the liver, gene expression changes resulting from the atherogenic diet were monitored. Ovariectomized C57BL/6 mice were fed either a chow or atherogenic diet and treated daily with EE (0.01 mg/kg) or test compound (Table 2). Real time RT-PCR analysis confirmed the atherogenic diet induction of mRNA for MHC invariant chain; VCAM-1, RANTES, and TNF-α and treatment with and the test compounds strongly suppressed the induction of these genes.

TABLE 2

Effects test compound on NF-κB target gene expression in C57BL/6 mice fed a high fat diet.

| Example # | conc mg/kg | RANTES % inhib (eff %) | VCAM-1 % inhib (eff %) | TNFa % inhib (eff %) | MHC % inhib (eff %) |
|---|---|---|---|---|---|
| 4 | 10 | 67 (151) | 59 (100) | 45 (100) | 60 (138) |

More importantly, treatment with the test compounds did not result in a significant induction in uterine wet weight increase, an undesirable activity associated with estrogen. The test compound administered at a dose of 10 mg/kg/day exhibited no effect on uterine wet weight increase in C57BL/6 compared to vehicle control.

These results suggest an anti-inflammatory role for the test compounds in terms of their ability to block inflammatory gene expression, with the desired selectivity in activity since no induction in uterine wet weights was observed.

Evaluation of Test Compound Using an ERE-reporter Test Procedure in MCF-7 BreastCancer Cells Stock solutions of test compounds (usually 0.1 M) are prepared in DMSO and then diluted 10 to 100-fold with DMSO to make working solutions of 1 or 10 mM. The DMSO stocks are stored at either 4° C. (0.1 M) or −20° C. (<0.1M). MCF-7 cells are passaged twice a week with growth medium [D-MEM/F-12 medium containing 10% (v/v) heat-inactivated fetal bovine serum, 1% (v/v) Penicillin-Streptomycin, and 2 mM glutaMax-1]. The cells are maintained in vented flasks at 37° C. inside a 5% $CO_2$/95% humidified air incubator. One day prior to treatment, the cells are plated with growth medium at 25,000 cells/well into 96 well plates and incubated at 37° C. overnight.

The cells are infected for 2 hr at 37° C. with 50 μl/well of a 1:10 dilution of adenovirus 5-ERE-tk-luciferase in experimental medium [phenol red-free D-MEM/F-12 medium containing 10% (v/v) heat-inactived charcoal-stripped fetal bovine serum, 1% (v/v) Penicillin-Streptomycin, 2 mM glutaMax-1, 1 mM sodium pyruvate]. The wells are then washed once with 150 μl of experimental medium. Finally, the cells are treated for 24 hr at 37° C. in replicates of 8 wells/treatment with 150 μl/well of vehicle (≦0.1% v/v DMSO) or compound that is diluted≧1000-fold into experimental medium.

Initial screening of test compounds is done at a single dose of 1 μM that is tested alone (estrogen receptor agonist mode) or in combination with 0.1 nM 17β-estradiol ($EC_{80}$; estrogen receptor antagonist mode). Each 96 well plate also includes a vehicle control group (0.1% v/v DMSO) and an estrogen receptor agonist control group (either 0.1 or 1 nM 17β-estradiol). Dose-response experiments are performed in either the estrogen receptor agonist and/or estrogen receptor antagonist modes on active compounds in log increases from $10^{-14}$ to $10^{-5}$ M. From these dose-response curves, $EC_{50}$ and $IC_{50}$ values, respectively, are generated. The final well in each treatment group contains 5 μl of $3\times10^{-5}$ M ICI-182,780 ($10^{-6}$ M final concentration) as an estrogen receptor antagonist control.

After treatment, the cells are lysed on a shaker for 15 min with 25 μl/well of 1× cell culture lysis reagent (Promega Corporation). The cell lysates (20 μl) are transferred to a 96 well luminometer plate, and luciferase activity is measured in a MicroLumat LB 96 P luminometer (EG & G Berthold) using 100 μl/well of luciferase substrate (Promega Corporation). Prior to the injection of substrate, a 1 second background measurement is made for each well. Following the injection of substrate, luciferase activity is measured for 10 seconds after a 1 second delay. The data are transferred from the luminometer to a Macintosh personal computer and analyzed using the JMP software (SAS Institute); this program subtracts the background reading from the luciferase measurement for each well and then determines the mean and standard deviation of each treatment.

The luciferase data are transformed by logarithms, and the Huber M-estimator is used to down-weight the outlying transformed observations. The JMP software is used to analyze the transformed and weighted data for one-way ANOVA (Dunnett's test). The compound treatments are compared to the vehicle control results in the estrogen receptor agonist mode, or the positive estrogen receptor agonist control results (0.1 nM 17β-estradiol) in the estrogen receptor antagonist mode. For the initial single dose experiment, if the compound treatment results are significantly different from the appropriate control ($p<0.05$), then the results are reported as the percent relative to the 17β-estradiol control [i.e., ((compound−vehicle control)/(17β-estradiol control−vehicle control))×100]. The JMP software is also used to determine the $EC_{50}$ and/or $IC_{50}$ values from the non-linear dose-response curves.

Evaluation of Uterotrophic Activity

Uterotrophic activity of a test compound can be measured according to the following standard pharmacological test procedures.

Procedure 1: Sexually immature (18 days of age) Sprague-Dawley rats are obtained from Taconic and provided unrestricted access to a casein-based diet (Purina Mills 5K96C) and water. On day 19, 20 and 21 the rats are dosed subcutaneously with 17α-ethinyl-17β-estradiol (0.06 μg/rat/day), test compound or vehicle (50% DMSO/50% Dulbecco's PBS). To assess estrogen receptor antagonist, compounds are coadministered with 17α-ethinyl-17β-estradiol (0.06 μg/rat/day). There are six rats/group and they are euthanized approximately 24 hours after the last injection by $CO_2$ asphyxiation and pneumothorax. Uteri are removed and weighed after trimming associated fat and expressing any internal fluid. A tissue sample can also be snap frozen for analysis of gene expression (e.g. complement factor 3 mRNA).

Procedure 2: Sexually immature (18 days of age) 129 SvE mice are obtained from Taconic and provided unrestricted access to a casein-based diet (Purina Mills 5K96C) and water. On day 22, 23, 24 and 25 the mice are dosed subcutaneously with compound or vehicle (corn oil). There are six mice/group and they are euthanized approximately 6 hours after the last injection by $CO_2$ asphyxiation and pneumothorax. Uteri are removed and weighed after trimming associated fat and expressing any internal fluid.

Evaluation of Osteoporosis and Lipid Modulation (Cardioprotection)

Female Sprague-Dawley rats, ovariectomized or sham operated, are obtained 1 day after surgery from Taconic Farms (weight range 240-275 g). They are housed 3 or 4 rats/cage in a room on a 12/12 (light/dark) schedule and provided with food (Purina 5K96C rat chow) and water ad libitum. Treatment for all studies begin 1 day after arrival and rats are dosed 7 days per week as indicated for 6 weeks. A group of age matched sham operated rats not receiving any treatment serve as an intact, estrogen replete control group for each study.

All test compounds are prepared in a vehicle of 50% DMSO (JT Baker, Phillipsburg, N.J.)/1× Dulbecco's phosphate saline (GibcoBRL, Grand Island, N.Y.) at defined concentrations so that the treatment volume is 0.1 mL/100 g body weight. 17β-estradiol is dissolved in corn oil (20 μg/mL) and delivered subcutaneously, 0.1 mL/rat. All dosages are adjusted at three week intervals according to group mean body weight measurements, and given subcutaneously.

Five weeks after the initiation of treatment and one week prior to the termination of the study, each rat is evaluated for bone mineral density (BMD). The total and trabecular density of the proximal tibia are evaluated in anesthetized rats using an XCT-960M (pQCT; Stratec Medizintechnik, Pforzheim, Germany). The measurements are performed as follows: Fifteen minutes prior to scanning, each rat is anesthetized with an intraperitoneal injection of 45 mg/kg ketamine, 8.5 mg/kg xylazine, and 1.5 mg/kg acepromazine.

The right hind limb is passed through a polycarbonate tube with a diameter of 25 mm and taped to an acrylic frame with the ankle joint at a 90° angle and the knee joint at 180°. The polycarbonate tube is affixed to a sliding platform that maintains it perpendicular to the aperture of the pQCT. The platform is adjusted so that the distal end of the femur and the proximal end of the tibia is in the scanning field. A two dimensional scout view is run for a length of 10 mm and a line resolution of 0.2 mm. After the scout view is displayed on the monitor, the proximal end of the tibia is located. The pQCT scan is initiated 3.4 mm distal from this point. The pQCT scan is 1 mm thick, has a voxel (three dimensional pixel) size of 0.140 mm, and consists of 145 projections through the slice.

After the pQCT scan is completed, the image is displayed on the monitor. A region of interest including the tibia but excluding the fibula is outlined. The soft tissue is mathematically removed using an iterative algorithm. The density of the remaining bone (total density) is reported in $mg/cm^3$. The outer 55% of the bone is mathematically peeled away in a concentric spiral. The density of the remaining bone (Trabecular density) is reported in $mg/cm^3$.

One week after BMD evaluation the rats are euthanized by $CO_2$ asphyxiation and pneumothorax, and blood is collected for cholesterol determination. The uteri are also removed and the weighed after trimming associated fat and expressing any luminal fluid. Total cholesterol is determined using a Boehringer-Mannheim Hitachi 911 clinical analyzer using the Cholesterol/HP kit. Statistics were compared using one-way analysis of variance with Dunnet's test.

Evaluation of Antioxidant Activity

Porcine aortas are obtained from an abattoir, washed, transported in chilled PBS, and aortic endothelial cells are harvested. To harvest the cells, the intercostal vessels of the aorta are tied off and one end of the aorta clamped. Fresh, sterile filtered, 0.2% collagenase (Sigma Type I) is placed in the vessel and the other end of the vessel then clamped to form a closed system. The aorta is incubated at 37° C. for 15-20 minutes, after which the collagenase solution is collected and centrifuged for 5 minutes at 2000×g. Each pellet is suspended in 7 mL of endothelial cell culture medium consisting of phenol red free DMEM/Ham's F12 media supplemented with charcoal stripped FBS (5%), NuSerum (5%), L-glutamine (4 mM), penicillin-streptomycin (1000 U/ml, 100 μg/ml) and gentamycin (75 μg/ml), seeded in 100 mm petri dish and incubated at 37° C. in 5% $CO_2$. After 20 minutes, the cells are rinsed with PBS and fresh medium added, this was repeated again at 24 hours. The cells are confluent after approximately 1 week. The endothelial cells are routinely fed twice a week and, when confluent, trypsinized and seeded at a 1:7 ratio. Cell mediated oxidation of 12.5 μg/mL LDL is allowed to proceed in the presence of the compound to be evaluated (5

μM) for 4 hours at 37° C. Results are expressed as the percent inhibition of the oxidative process as measured by the TBARS (thiobarbituric acid reactive substances) method for analysis of free aldehydes [Yagi, *Biochemical Medicine* 15: 212-6 (1976)].

Progesterone Receptor mRNA Regulation Standard Pharmacological Test Procedure

This test procedure can be used to evaluate the estrogenic or antiestrogenic activity of compounds from this invention [Shughrue, et al., *Endocrinology* 138: 5476-5484 (1997)].

Rat Hot Flush Test Procedure

The effect of test compounds on hot flushes can be evaluated in a standard pharmacological test procedure which measures the ability of a test compound to blunt the increase in tail skin temperature which occurs as morphine-addicted rats are acutely withdrawn from the drug using naloxone [Merchenthaler, et al., *Maturitas* 30: 307-16 (1998)]. It can also be used to detect estrogen receptor antagonist activity by co-dosing test compound with the reference estrogen.

Evaluation of Vasomotor Function in Isolated Rat Aortic Rings

Sprague-Dawley rats (240-260 grams) are divided into 4 groups:
1. Normal non-ovariectomized (intact)
2. Ovariectomized (ovex) vehicle treated
3. Ovariectomized 17β-estradiol treated (1 mg/kg/day)
4. Ovariectomized animals treated with test compound (various doses)

Animals are ovariectomized approximately 3 weeks prior to treatment. Each animal receives either 17-β estradiol sulfate (1 mg/kg/day) or test compound suspended in distilled, deionized water with 1% tween-80 by gastric gavage. Vehicle treated animals received an appropriate volume of the vehicle used in the drug treated groups.

Animals are euthanized by $CO_2$ inhalation and exsanguination. Thoracic aortae are rapidly removed and placed in 37° C. physiological solution with the following composition (mM): NaCl (54.7), KCl (5.0), $NaHCO_3$ (25.0), $MgCl_2$ $2H_2O$ (2.5), D-glucose (11.8) and $CaCl_2$ (0.2) gassed with $CO_2$—$O_2$, 95%/5% for a final pH of 7.4. The advantitia is removed from the outer surface and the vessel is cut into 2-3 mm wide rings. Rings are suspended in a 10 mL tissue bath with one end attached to the bottom of the bath and the other to a force transducer. A resting tension of 1 gram is placed on the rings. Rings are equilibrated for 1 hour, signals are acquired and analyzed.

After equilibration, the rings are exposed to increasing concentrations of phenylephrine ($10^{-8}$ to $10^{-4}$ M) and the tension recorded. Baths are then rinsed 3 times with fresh buffer. After washout, 200 mM L-NAME is added to the tissue bath and equilibrated for 30 minutes. The phenylephrine concentration response curve is then repeated.

Evaluation of Cardioprotective Activity

Apolipoprotein E-deficient C57/B1J (apo E KO) mice are obtained from Taconic Farms. All animal procedures are performed under strict compliance to IACUC guidelines. Ovariectomized female apo E KO mice, 4-7 weeks of age, are housed in shoe-box cages and were allowed free access to food and water. The animals are randomized by weight into groups (n=12-15 mice per group). The animals are dosed with test compounds or estrogen (17β-estradiol sulfate at 1 mg/kg/day) in the diet using a Precise-dosing Protocol, where the amount of diet consumed is measured weekly, and the dose adjusted accordingly, based on animal weight. The diet used is a Western-style diet (57U5) that is prepared by Purina and contains 0.50% cholesterol, 20% lard and 25 IU/KG Vitamin E. The animals are dosed/fed using this paradigm for a period of 12 weeks. Control animals are fed the Western-style diet and receive no compound. At the end of the study period, the animals are euthanized and plasma samples obtained. The hearts are perfused in situ, first with saline and then with neutral buffered 10% formalin solution.

For the determination of plasma lipids and lipoproteins, total cholesterol and triglycerides are determined using enzymatic methods with commercially available kits from Boehringer Mannheim and Wako Biochemicals, respectively and analyzed using the Boehringer Mannheim Hitachii 911 Analyzer. Separation and quantification of plasma lipoproteins were performed using FPLC size fractionation. Briefly, 50-100 mL of serum is filtered and injected into Superose 12 and Superose 6 columns connected in series and eluted at a constant flow rate with 1 mM sodium EDTA and 0.15 M NaCl. Areas of each curve representing VLDL, LDL and HDL are integrated using Waters Millennium™ software, and each lipoprotein fraction is quantified by multiplying the Total Cholesterol value by the relative percent area of each respective chromatogram peak.

For the quantification of aortic atherosclerosis, the aortas are carefully isolated and placed in formalin fixative for 48-72 hours before handling. Atherosclerotic lesions are identified using Oil Red O staining. The vessels are briefly destained, and then imaged using a Nikon SMU800 microscope fitted with a Sony 3CCD video camera system in concert with IMAQ Configuration Utility (National Instrument) as the image capturing software. The lesions are quantified en face along the aortic arch using a custom threshold utility software package (Coleman Technologies). Automated lesion assessment is performed on the vessels using the threshold function of the program, specifically on the region contained within the aortic arch from the proximal edge of the brachio-cephalic trunk to the distal edge of the left subclavian artery. Aortic atherosclerosis data are expressed as percent lesion involvement strictly within this defined luminal area.

Evaluation of Cognition Enhancement

Ovariectomized rats (n=50) are habituated to an 8-arm radial arm maze for 10-min periods on each of 5 consecutive days. Animals are water-deprived prior to habituation and testing. A 100 μL aliquot of water placed at the ends of each arm serves as reinforcement. Acquisition of a win-shift task in the radial arm maze is accomplished by allowing the animal to have access to one baited arm. After drinking, the animal exits the arm and re-enters the central compartment, where it now has access to the previously visited arm or to a novel arm. A correct response is recorded when the animal chooses to enter a novel arm. Each animal is given 5 trials per day for 3 days. After the last acquisition trial, the animals are assigned to one of the following 4 groups:
1. Negative controls: injected with 10% DMSO/sesame oil vehicle once daily for 6 days (1 mL/kg, SC)
2. Positive controls: injected with 17β-estradiol benzoate for 2 days and tested 4 days after the second injection (17β-estradiol benzoate at 10 μg/0.1 mL per rat)
3. Estradiol: 17β-estradiol will be injected daily for 6 days (20 μg/kg, SC)
4. Test compound: injected daily for 6 days (doses vary).

All injections will begin after testing on the last day of acquisition. The last injection for groups 1, 3, and 4 will take place 2 hours before testing for working memory.

The test for working memory is a delayed non-matching-to-sample task (DNMS) utilizing delays of 15, 30, or 60 seconds. This task is a variation of the acquisition task in which the rat is placed in the central arena and allowed to enter one arm as before. A second arm is opened once the rat traverses halfway down the first arm, and again the rat is required to choose this arm. When it has traveled halfway down this second arm, both doors are closed and the delay is instituted. Once the delay has expired, both of the original two doors, and a third novel door, are opened simultaneously. A correct response is recorded when the animal travels halfway down the third, novel arm. An incorrect response is recorded when the animal travels halfway down either the first or second arms. Each animal will receive 5 trials at each of the three delay intervals for a total of 15 trials per subject.

Evaluation of Effect on Pleurisy

The ability to reduce the symptoms of experimentally-induced pleurisy in rats can be evaluated according to the procedure of Cuzzocrea [*Endocrinology* 141: 1455-63 (2000)].

Evaluation of Protection Against Glutamate-induced Cytotoxicity (Neuroprotection)

The neuroprotective activity of compounds of this invention can be evaluated in an in vitro standard pharmacological test procedure using glutamate challenge [Zaulyanov, et al., *Cellular & Molecular Neurobiology* 19: 705-18 (1999); Prokai, et al., *Journal of Medicinal Chemistry* 44: 110-4 (2001)].

Evaluation in the Mammary End Bud Test Procedure

Estrogens are required for full ductal elongation and branching of the mammary ducts, and the subsequent development of lobulo-alveolar end buds under the influence of progesterone. In this test procedure, the mammotrophic activity of selected compounds of the invention can be evaluated according to the following standard pharmacological test procedure. Twenty-eight day old Sprague-Dawley rats (Taconic Farms, Germantown, N.Y.) are ovariectomized and rested for nine days. Animals are housed under a 12-hour light/dark cycle, fed a casein-based Purina Laboratory Rodent Diet 5K96 (Purina, Richmond, Ind.) and allowed free access to water. Rats were then dosed subcutaneously for six days with vehicle (50% DMSO (J T Baker, Phillipsburg, N.J.)/50% 1× Dulbecco's Phosphate buffered saline (GibcoBRL, Grand Island, N.Y.), 17β-estradiol (0.1 mg/kg) or test compound (20 mg/kg). For the final three days, rats are also dosed subcutaneously with progesterone (30 mg/kg). On the seventh day, rats are euthanised and a mammary fat pad excised. This fat pad is analyzed for casein kinase II mRNA as a marker of end bud proliferation. Casein kinase II mRNA is analyzed by real-time RT-PCR. Briefly, RNA is isolated following Trizol (GibcoBRL, Grand Island, N.Y.) according to the manufacture's directions, Samples are treated with DNAse I using DNA-free kit (Ambion), and casein kinase II mRNA levels are measured by real-time RT-PCR using the Taqman Gold procedure (PE Applied Biosystems). A total of 50 ng of RNA is analyzed in triplicate using casein kinase II specific primer pair (5' primer, CACACGGATGGCGCATACT; SEQ ID NO. 1; 3' primer, CTCGGGATGCACCATGAAG, SEQ ID NO. 2) and customized probe (TAMRA-CGGCACTGGTTTCCCT-CACATGCT-FAM, SEQ ID NO. 3). Casein kinase II mRNA levels are normalized to 18s ribosomal RNA contained within each sample reaction using primers and probe supplied by PE Applied Biosystems.

Evaluation in the HLA Rat Standard Pharmacological Test Procedure for Inflammatory Bowel Disease Representative compounds can be evaluated in the HLA rat standard pharmacological test procedure which emulates inflammatory bowel disease in humans. The following briefly describes the procedure used and results obtained. Male HLA-B27 rats are obtained from Taconic and provided unrestricted access to food (PMI Lab diet 5001) and water. Rats are dosed subcutaneously once per day with either vehicle (50% DMSO/50% 1× Dulbecco's Phosphate Buffered Saline) or test compound (0.1 to 10 mg/kg) for at least one week. Stool quality is observed daily and graded according to the following scale: Diarrhea=3; soft stool=2; normal stool=1. At the end of the study, serum is collected and stored at $-70°$ C. A section of colon is prepared for histological analysis and an additional segment is analyzed for myeloperoxidase activity.

For histological analysis, colonic tissue is immersed in 10% neutral buffered formalin. Each specimen of colon is separated into four samples for evaluation. The formalin-fixed tissues are processed in a Tissue Tek vacuum infiltration processor (Miles, Inc; West Haven, Conn.) for paraffin embedding. The samples are sectioned at 5 μm and then stained with hematoxylin and eosin (H&E) for blinded histologic evaluations using a scale modified after Boughton-Smith. After the scores are completed the samples are unblinded, and data are tabulated and analyzed by ANOVA linear modeling with multiple mean comparisons. Sections of colonic tissue are evaluated for several disease indicators and given relative scores.

Evaluation in Three Models of Arthritis

Lewis rat assay of adjuvant-induced arthritis. Sixty, female, 12 weeks old, Lewis rats are housed according to standard facility operating procedures. They receive a standard regimen of food and water ad libitum. Each animal is identified by a cage card indicating the project group and animal number. Each rat number is marked by indelible ink marker on the tail. At least 10-21 days before study they are anesthetized and ovariectomized by standard aseptic surgical techniques.

Freund's Adjuvant-Complete (Sigma Immuno Chemicals, St. Louis, Mo.) is used to induce arthritis, each mL containing 1 mg *Mycobacterium tuberculosis* heat killed and dried, 0.85 mL mineral oil and 0.15 mL mannide monooleate Lot No. 084H8800.

The following are examples of two test procedures. Inhibition test procedure: Thirty rats are injected intradermally with 0.1 mL of Freund's Adjuvant-Complete at the base of the tail. The animals are randomized to four groups, each group containing six rats. Each day, the groups receive vehicle (50% DMSO (JT Baker, Phillipsburg, N.J.)/1× Dulbecco's phosphate saline (GibcoBRL, Grand Island, N.Y.)) or test compound (0.1-10 mg/kg, administered subcutaneously). All rats begin treatment on Day 1.

Treatment test procedure: Thirty rats are injected intradermally with 0.1 mL of Freund's Adjuvant-Complete at the base of the tail. The animals are randomized to four groups, each group containing six rats. Each day, the groups receive vehicle (50% DMSO (JT Baker, Phillipsburg, N.J.)/1× Dulbecco's phosphate saline (GibcoBRL, Grand Island, N.Y.)) or test compound (0.1-10 mg/kg, administered subcutaneously). All rats begin treatment on Day 8 after adjuvant injection.

Statistical analysis is performed using Abacus Concepts SuperANOVA. (Abacus Concepts, Inc., Berkeley, Calif.). All of the parameters of interest are subjected to Analysis of Variance with Duncan's new multiple range post hoc testing between groups. Data are expressed throughout as mean±standard deviation (SD), and differences are deemed significant if $p<0.05$.

The degree of arthritis severity is monitored daily in terms of the following disease indices: Hindpaw erythema, hindpaw swelling, tenderness of the joints, and movements and posture. An integer scale of 0 to 3 is used to quantify the level of erythema (0=normal paw, 1=mild erythema, 2=moderate erythema, 3=severe erythema) and swelling (0=normal paw, 1=mild swelling, 2=moderate swelling, 3=severe swelling of the hind paw). The maximal score per day is 12.

At the end of the study the rats are euthanized with $CO_2$, hindlimbs removed at necropsy and fixed in 10% buffered formalin, and the tarsal joints decalcified and embedded in paraffin. Histologic sections are stained with Hematoxylin and Eosin or Saffranin O—Fast Green stain.

Slides are coded so that the examiner is blinded to the treatment groups. Synovial tissue from tarsal joints is evaluated based on synovial hyperplasia, inflammatory cell infiltration, and pannus formation [*Poole and Coombs, International Archives of Allergy & Applied Immunology* 54: 97-113 (1977)] as outlined below.

| Category | Grade |
| --- | --- |
| 1. Synovial lining cells | |
| a. No change | 0 |
| b. Cells enlarged, slightly thickened | 1 |
| c. Cells enlarged, increase in numbers, moderately thickened. No villus present | 2 |
| d. Cells enlarged, thickened. Villlus present | 3 |
| 2. Fibroplasia | |
| a. No change | 0 |
| b. Fibroplasia present under lining cells | 1 |
| c. Small areas of areolar tissue replaced by fibrous tissue | 2 |
| d. Replacement of areolar tissue by fibrous tissue | 3 |
| 3. Inflammatory cells | |
| a. Occasionally seen, scattered throughout selection | 0 |
| b. Cells present in small numbers in or just under lining cell layer and/or around blood vessels. | 1 |
| c. Small focal collection of cells may be present | 2 |
| d. Large numbers of cells present in capsule and in or under lining cell layers. Large foci often seen. | 3 |
| 4. Pannus | |
| a. Not detectable | 0 |
| b. Detectable | 1 |

In addition, articular cartilage and bone is evaluated using Mankin's histological grading system [Mankin, et al., *Journal of Bone & Joint Surgery—American Volume* 53: 523-37 (1971)] as shown below.

| II. Category | Grade |
| --- | --- |
| 1. Structure | |
| a. Normal | 0 |
| b. Surface irregularity | 1 |
| c. Pannus and surface irregularity | 2 |
| d. Clefts to transitional zone | 3 |
| e. Clefts to radial zone | 4 |
| f. Clefts to calcified zone | 5 |
| g. Complete disorganization | 6 |
| 2. Cells | |
| a. Normal | 0 |
| b. Diffuse hypercellularity | 1 |
| c. Cloning | 2 |
| d. Hypocellularity | 3 |
| 3. Safranin-O staining | |
| a. Normal | 0 |
| b. Slight reduction | 1 |
| c. Modest reduction | 2 |
| d. Severe reduction | 3 |
| e. No dye noted | 4 |
| 4. Tidemark integrity | |
| a. Intact | 0 |
| b. Crossed by blood vessels | 1 |

Evaluation in the HLA-B27 Rat Model of Arthritis.

Representative compounds are evaluated in the HLA-B27 rat standard pharmacological test procedure which emulates arthritis in humans. The following briefly describes the procedure used. Male HLA-B27 rats are obtained from Taconic and provided unrestricted access to a food (PMI Lab diet 5001) and water. Rats are dosed subcutaneously once per day with either vehicle (50% DMSO/50% 1× Dulbecco's Phosphate Buffered Saline) or test compound (0.1 to 10 mg/kg) for at least one week. Joint scores and histology are evaluated as described above for the Lewis rat model of adjuvant-induced arthritis.

Evaluation in the Collagen Induced Arthritis Models.

Compounds are evaluated in BALB/c mice, 6-8 weeks of age, in which arthritis is induced by monoclonal antibodies raised against type II collagen, plus lipopolysaccharide (LPS). The animals were administered intravenously with a combination of 4 different mAbs totaling 4 mg/mouse on day 0, and followed by intravenous 25 μg of LPS 72 hours later (day 3). From day 3, one hour after LPS application, tested compounds are give orally once daily for 15 days. For each animal, increase in volume of both hind paws is measured using a plethysmometer with water cell (12 mm diameter) on days 0, 5, 7, 10, 14 and 17. Percent inhibition of increase in volume is calculated.

Evaluation in In Vivo Models of Carcinogeneisis

The ability of compounds of this invention to treat and inhibit various malignancies or hyperprolific disorders can be evaluated in standard pharmacological test procedures that are readily available in the literature, and include the following two procedures.

Breast cancer. Athymic nu/nu (nude) mice are obtained ovariectomized from Charles River Laboratories (Wilmington, Mass.). One day prior to tumor cell injection, animals are implanted with time-release pellets containing 0.36-1.7 mg 17β-estradiol (60 or 90 day release, Innovative Research of America, Sarasota, Fla.) or a placebo. The pellet is introduced subcutaneously into the intrascapular region using a 10-gauge precision trochar. Subsequently, mice are injected subcutaneously into the breast tissue with either $1 \times 10^7$ MCF-7 cells or $1 \times 10^7$ BG-1 cells. The cells are mixed with an equal volume of matrigel, a basement membrane matrix preparation to enhance tumor establishment. Test compounds can be evaluated either by dosing one day after tumor cell implantation (inhibition regimen) or after tumors have reached a certain size (treatment regimen). Compounds are administered either intraperitoneally or orally in a vehicle of 1% tween-80 in saline each day. Tumor size is evaluated every three or seven days.

Colon cancer. The ability to treat or inhibit colon cancer can be evaluated in the test procedure of Smirnoff [*Oncology Research* 11: 255-64 (1999)].

Evaluation of Neuroprotection in Two In Vivo Test Procedures

Transient global ischemia in the Mongolian gerbil. The effect of test compounds on preventing or treating brain injury in response to oxygen deprivation/reperfusion can be measured using the following test procedure.

Female Mongolian gerbils (60-80 g; Charles River Laboratories, Kingston, N.Y.) are housed in the Wyeth-Ayerst animal care facility (AAALAC certified) with a 12-hour light, 12-hour dark photoperiod and free access to tap water and a low-estrogen casein diet (Purina; Richmond, Ind.). After acclimation (3-5 days), gerbils are anesthetized with isoflurane (2-3% mixture with $O_2$), ovariectomized (Day 0). Beginning the following morning (Day 1), gerbils are treated subcutaneously each day with either vehicle (10% ETOH/corn oil), 17β-estradiol (1 mg/kg) or an experimental compound (0.1-20 mg/kg). On Day 6, gerbils (n=4-5/group) are anesthetized with isoflurane, the common carotid arteries visualized via a mid-line neck incision and both arteries simultaneously occluded for 5 minutes with non-traumatic micro aneurysm clips. After occlusion, the clips are removed to allow cerebral reperfusion and the neck incision closed with wound clips. All animals are fasted overnight prior to the global ischemia surgery, a step that facilitates consistent ischemic injury. On Day 12, gerbils are exposed to a lethal dose of $CO_2$, and the brains frozen on dry ice and stored at −80° C.

The degree of neuronal protection is evaluated by in situ hybridization analysis of neurogranin mRNA. Briefly, 20 µm coronal cryostat sections are collected on gelatin-coated slides, dried and stored at −80° C. At the time of processing, the desiccated slide boxes are warmed to room temperature, the slides postfixed in 4% paraformaldehyde, treated with acetic anhydride and then delipidated and dehydrated with chloroform and ethanol. Processed section-mounted slides are then hybridized with 200 µl ($6 \times 10^6$ DPM/slide) of an antisense or sense (control) riboprobe for Neurogranin ($^{35}$S-UTP-labeled NG-241; bases 99-340). in a 50% formamide hybridization mix and incubated overnight at 55° C. in a humidified slide chamber without coverslipping. The following morning, the slides are collected in racks, immersed in 2×SSC (0.3 M NaCl, 0.03 M sodium citrate; pH 7.0)/10 mM DTT, treated with RNase A (20 µg/ml) and washed (2×30 min) at 67° C. in 0.1×SSC to remove nonspecific label. After dehydration, the slides are opposed to BioMax (BMR-1; Kodak) X-ray film overnight.

The level of neurogranin hybridization signal is used to quantitatively assess the degree of neuronal loss in the CA1 region after injury and to evaluate the efficacy of 17β-estradiol and experimental compounds. Neurogranin mRNA is selected for these studies because it is highly expressed in the hippocampal neurons including CA1, but absent in glia and other cell types present in this brain region. Therefore, measurement of the amount of neurogranin mRNA present represents surviving neurons. Relative optical density measurements of neurogranin hybridization signal are obtained from film autoradiograms with a computer based image analysis system (C-Imaging Inc., Pittsburgh, Pa.). The results from 6 sections (40 µm apart) per animal are averaged and statistically evaluated. Numerical values are reported as the mean±SEM. One-way analysis of variance is used to test for differences in the level of neurogranin mRNA and all statements of non-difference in the results section imply that p>0.05.

Middle cerebral artery occlusion in mice. Neuroprotection can be evaluated according to the test procedures described by Dubal [see, Dubal, et al., *Proceedings of the National Academy of Sciences of the United States of America* 98: 1952-1957 (2001), Dubal, et al., *Journal of Neuroscience* 19: 6385-6393 (1999)].

Ovulation Inhibition Standard Pharmacological Test Procedure

The test procedure is used to determine whether test compounds can inhibit or change the timing of ovulation. It can also be used to determine the number of oocytes ovulated [Lundeen, et al., *J. Steroid Biochem. Mol. Biol.* 78: 137-143 (2001)].

Transplantation Rejection

To test the ability of the test compounds to prevent transplant rejection. Compounds can be tested in animal models of heart transplantation (Stetson et al. Circulation 104:676-682 (2001) or transplant atherosclerosis (Deitrich et al. *Arterioscler. Thromb. Vasc Biol.* 20:343-352 (2000), Lou et al., *Circulation* 94:3355-3361 (1996).

Prevention of Restenosis

The test procedure is used to determine whether test compounds can inhibit vascular smooth muscle cell proliferation after carotid artery injury similar to what occurs after balloon angioplasty. The test compounds can be tested in animal models previously described (Karas et al. *Circ Res.* 89:534-539 (2001), Cerek et al. *Atherosclerosis* 131:59-66 (1997).

Treatment of Myocardial Infarction

Test compounds can be tested in animal models of ischemia/reperfusion to determine whether they would inhibit cell death occurring during a myocardial infarction. The compounds can be tested in models described previously (Delyani et al. *J. Mol. & Cell Cardiology* 28:1001-1008 (1996), Izumi et al. *J. Clin. Invest.* 108:203-213 (2001) & Chandrasekar et al. *Circulation* 103:2296-2302 (2001)).

Treatment for Myocarditis and Congestive Heart Failure

Test compounds can be tested in models of heart failure to determine whether compounds could be an effective therapy and improve cardiac function. Compounds can be tested in animals as described previously (Yokoseki et al. *Circ Res.* 89:1-9 (2001), Wallen et al. *Hypertension* 36:774-779 (2000) & Toshiaki et al. *Circulation* 104:1094-1103 (2001)).

Treatment for Diabetes

Test compounds can be tested in models of diabetes to determine their effect on reversal of obesity and diet-induced insulin resistance. Compounds can be tested in animal models as previously described (Yuan et al. *Science* 293:1673-1677 (2001).

Treatment for Asthma

Pulmonary Inflammation Model Sensitize mice with OVA emulsified in alum on days 0 and 14 (ip injection). On days 28 and 29, challenge with an aerosol of OVA for 20 min (1%-5% OVA) and then on Day 30 the animals are sacrificed and harvest BAL and/or lung tissue for analysis of pulmonary inflammation.

Airway Hyperresponsiveness. This model is similar to that described above however animals are challenged on 3 consecutive days with an aerosol of OVA and airway hyperresponsiveness is measured 48 h after the last challenge. BAL can also be taken at this stage if required.

To look more directly at the effects of mast cells in conjunction with ER, may use a passive cutaneous anaphylaxis model in which IgE is injected into the ear and then 24 hours later inject DNP-HSA iv. Measure ear thickness and an early and late phase reaction. Furthermore, fix tissues in K2 and embed in Epoxy resin and cut 1 um sections. These can be stained for mast cells and quantitiate the degree of mast cell degranulation.

Based on the results obtained in the standard pharmacological test procedures, the compounds of this invention are selective anti-inflammatory compounds described herein useful for the treatment and prevention of chronic inflammatory diseases without stimulating uterine and breast cell proliferation as found with classic estrogens.

Accordingly, the compounds of this invention are useful in treating or inhibiting osteoporosis and in the inhibition of bone demineralization, which may result from an imbalance in a individual's formation of new bone tissues and the resorption of older tissues, leading to a net loss of bone. Such bone depletion results in a range of individuals, particularly in post-menopausal women, women who have undergone bilateral oophorectomy, those receiving or who have received extended corticosteroid therapies, those experiencing gonadal dysgenesis, and those suffering from Cushing's syndrome. Special needs for bone, including teeth and oral bone, replacement can also be addressed using these compounds in individuals with bone fractures, defective bone structures, and those receiving bone-related surgeries and/or the implantation of prosthesis. In addition to those problems described above, these compounds can be used in treatment or inhibition for osteoarthritis, hypocalcemia, hypercalcemia, Paget's disease, osteomalacia, osteohalisteresis, multiple myeloma and other forms of cancer having deleterious effects on bone tissues.

The compounds of this invention are also active in the brain and are therefore useful for inhibiting or treating Alzheimer's disease, cognitive decline, decreased libido, senile dementia, neurodegenerative disorders, depression, anxiety, insomnia, schizophrenia, and infertility. The compounds of this invention are also useful in treating or inhibiting benign or malignant abnormal tissue growth including, glomerulosclerosis, prostatic hypertrophy, uterine leiomyomas, breast cancer, scleroderma, fibromatosis, endometriosis, endometrial cancer, polycystic ovary syndrome, endometrial polyps, benign breast disease, adenomyosis, ovarian cancer, melanoma, prostate cancer, cancers of the colon, CNS cancers, such as glioma or astioblastomia.

The compounds of this invention are cardioprotective and are antioxidants, and are useful in lowering cholesterol, triglycerides, Lp(a), and LDL levels; inhibiting or treating hypercholesteremia, hyperlipidemia, cardiovascular disease, atherosclerosis, peripheral vascular disease, restenosis, and vasospasm, and inhibiting vascular wall damage from cellular events leading toward immune mediated vascular damage.

The compounds of this invention are also useful in treating disorders associated with inflammation or autoimmune diseases, including inflammatory bowel disease (Crohn's disease, ulcerative colitis, indeterminate colitis), arthritis (rheumatoid arthritis, spondyloarthropathies, osteoarthritis), pleurisy, ischemia/reperfusion injury (e.g. stroke, transplant rejection, myocardial infarction, etc.), asthma, giant cell arteritis, prostatitis, uveitis, psoriasis, multiple sclerosis, systemic lupus erythematosus and sepsis.

The compounds of this invention are also useful in treating or inhibiting ocular disorders including cataracts, uveitis, and macular degeneration and in treating skin conditions such as aging, alopecia, and acne.

The compounds of this invention are also useful in treating or inhibiting metabolic disorders such as type-II diabetes, of lipid metabolism, appetite (e.g. anorexia nervosa and bulimia).

Compounds in this invention are also useful in treating or inhibiting bleeding disorders such as hereditary hemorrhagic telangiectasia, dysfunctional uterine bleeding, and combating hemorrhagic shock. The compounds of this invention are useful in disease states where amenorrhea is advantageous, such as leukemia, endometrial ablations, chronic renal or hepatic disease or coagulation diseases or disorders.

The following examples are presented to illustrate rather than limit the scope of this invention. All NMR data was collected at 400 MHz, unless otherwise specified. Common abbreviations are used for solvents such as diethyl ether (Et$_2$O), methylene chloride (CH$_2$Cl$_2$), and ethyl acetate (EtOAc) known to one skilled in the art. Common abbreviations are used for aqueous solutions of acids and bases such as hydrochloric acid (HCl) and sodium hydride (NaOH) etc.

INTERMEDIATES

Intermediate 1

3-bromoindazole

The title compound was prepared as outlined in a procedure described by B. E. Boulton, B. A. Coller, *Aust. J. Chem.*, 1974, 27, 2343. To a mechanically stirred solution of indazole (5.0 g, 42 mmol) in 20% aq. NaOH (75 mL) was added bromine (1.4 mL, 27 mmol) dropwise. After stirring at ambient temperature for 2 h, the reaction mixture was cooled and acidified by careful addition of concentrated HCl. The solids formed were filtered and dried to give 5.5 g of the title compound.

$^1$H NMR (DMSO-d$_6$,300 MHz):δ 7.20 (t, 1H), 7.45 (t, 1H), 7.57 (d, 2H).

Intermediate 2

3-bromo-7-(trifluoromethyl)-1H-indazole

Step A: 7-(trifluoromethyl)-1H-indazole

A solution of 2-fluoro-3-trifluoromethylbenzaldehyde (5 g, 26 mmol)), hydrazine hydrate (8.3 mL, 260 mmol) and DMAP (3.17 g, 26 mmol.) in 10 mL pyridine was heated at 100° C. for 24 hours. The cool reaction mixture was partitioned with EtOAc and 1 N HCl. The organic phase was washed with brine and dried with anhydrous sodium sulfate (Na$_2$SO$_4$). The organic phase was concentrated in vacuo to give 4.5 g of product. The crude product was recrystallized from Et$_2$O/hexane to give the title compound (3.6 g, white solid, mp 90° C.).

$^1$H NMR (DMSO-d$_6$):δ 7.27 (t, 1H), 7.73 (d, 1H), 8.10 (d, 1H), 8.29 (d, 1H), 13.63 (s, 1H) MS (ESI) m/z 185 [M–H]$^-$

Step B: 3-bromo-7-(trifluoromethyl)-1H-indazole

To a mechanically stirred solution of 7-trifluoromethylindazole (3.5 g, 18.8 mmol) in 20% NaOH was added bromine (0.62 mL, 12.1 mmol) dropwise. After stirring at ambient temperature for 2 hours, the reaction mixture was cooled and acidified to pH 6-7 by careful addition of concentrated HCl. The solids formed were filtered and dried to give the title compound (2.9 g) as a white solid.

$^1$H NMR (DMSO-d$_6$): δ 7.39 (t, 1H), 7.86 (d, 1H), 7.91(d, 1H), 14.02 (s, 1H). MS (ESI) m/z 263 ([M–H]$^-$).

EXAMPLE 1

3-[(1H-indazol-3-yl)methyl]phenol

Step A:
[3-(benzyloxy)phenyl](1H-indazol-3-yl)methanol

A solution of 3-bromoindazole (3.2 g, 16.4 mmol) in 50 mL Et$_2$O was cooled to −78° C. and treated dropwise with n-butyllithium (6.6 mL, 16.4 mmol, 2.5M in hexanes). After the addition was complete, t-butyllithium (19 mL, 32.4 mmol, 1.7M in pentane) was added dropwise to the cooled solution. The mixture was stirred at −78° C. for 15 minutes after which 3-benzyloxyoxybenzaldehyde (3.8 g, 18 mmol) was added in one portion. The cooling bath was removed and the solution was allowed to warm to ambient temperature. The reaction was quenched with 1N HCl and extracted with EtOAc. The organic phase was washed with brine and dried (Na$_2$SO$_4$). Removal of the solvent afforded the crude product which was purified by flash chromatography (silica gel, hexane-ethyl acetate, 3:2) to give the title compound, 1.3 g off-white solid. mp 124-125° C.;

$^1$H NMR (DMSO-d$_6$): δ 5.05 (s, 2H), 6.03 (s, 2H), 6.83 (dd, 1H), 6.97 (m, 2H), 7.13 (s, 1H), 7.18 (t, 1H), 7.24-7.32 (m, 2H), 7.35 (t, 1H), 7.42 (m, 4H), 7.64 (d, 1H), 12.74 (s, 1H). MS (ESI) m/z 329 ([M−H]$^−$); Anal. calcd for C$_{21}$H$_{18}$N$_2$O$_2$: C:76.34; H:5.49 N:8.48 Found: C:75.90; H:5.47 N:8.41.

Step B: 3-(1H-indazol-3-ylmethyl)phenol

A mixture of [3-(benzyloxy)phenyl](H-indazol-3-yl) methanol (0.10 g, 0.3 mmol), ammonium formate (0.2 g, 3 mmol) and 10% palladium(0.085 g) on carbon in 10 mL ethanol was stirred at ambient temperature for 0.5 hours. The reaction was filtered (celite) and the filtrate concentrated in vacuo to give the crude product residue. Trituration with hexane afforded the title compound (0.053 g) as an off-white solid.

mp 170-172° C.; $^1$H NMR (DMSO-d$_6$): δ 4.15 (s, 2H), 6.54 (dd, 1H), 6.64 (s, 1H), 6.72 (d, 1H), 7.025 (m, 2H), 7.27 (t, 1H), 7.44 (d, 1H), 7.56 (d, 1H), 9.20 (s, 1H), 12.71 (s, 1H). MS (ESI) m/z 225 ([M+H]$^+$).

EXAMPLE 2

3-[hydroxy(1-propyl-1H-indazol-3-yl)methyl]phenol

Step A: [3-(benzyloxy)phenyl](1-propyl-1H-indazol-3-yl)methanol

A solution of [3-(benzyloxy)phenyl](H-indazol-3-yl) methanol (0.20 g, 0.6 mmol) in 2 mL DMF was added in one portion sodium hydride (0.024 g, 0.6 mmol, 60% in oil). After the gas evolution ceased, 1-iodopropane (0.098 mL, 1.0 mmol) was added and the reaction was stirred at ambient to 50° C. overnight. The cool reaction mixture was partitioned with EtOAc and 1 N HCl. The organic phase was washed with brine and dried (Na$_2$SO$_4$). The resulting residue was purified by HPLC chromatography through silica gel (column: 150× 12 mm (Biotage) at 10 mL/min with methyl-t-butyl ether/ hexane, gradient elution, 1:9 to 1:1) to give 0.083 g of the title compound.

$^1$H NMR (DMSO-d$_6$): δ 0.81 (t, 3H), 1.80 (m, 2H), 4.29 (t, 2H), 5.05 (s, 2H), 6.01 (m, 1H), 6.06 (m, 1H), 6.83 (dd, 1H), 6.98 (m, 2H), 7.12 (s, 1H), 7.18 (t, 1H), 7.31 (m, 2H), 7.35 (m, 2H), 7.39 (m, 2H), 7.56 (d, 1H), 7.63 (d, 1H). MS (ESI) m/z 373 ([M+H]$^+$);

Step B: 3-[hydroxy(1-propyl-1H-indazol-3-yl)methyl]phenol

A mixture of [3-(benzyloxy)phenyl]-(1-propyl-1H-indazol-3-yl)methanol (0.067 g, 0.18 mmol.), ammonium formate (0.09 g, 1.17 mmol) and 10% palladium on carbon (0.09 g) in 10 mL ethanol was heated at reflux for 18 hours. The reaction was filtered (celite) and the cake washed with excess ethanol. The filtrate was concentrated in vacuo. The crude product was purified by HPLC [column: silica gel 150×12 mm (Biotage) at 10 mL/min with methyl-t-butyl ether/hexane, gradient elution, 1:9 to 1:1 over 15 min) to give the title compound (0.018 g) as a white solid.

$^1$H NMR (DMSO-d$_6$): δ 0.83 (t, 3H), 1.81 (m, 2H), 4.29 (t, 2H), 5.94 (m, 1H), 5.96 (m, 1H), 6.55 (dd, 1H), 6.84 (d, 1H), 6.87 (s, 1H), 6.99 (t, 1H), 7.05 (t, 1H), 7.29 (t, 1H), 7.56 (d, 1H), 7.64 (d, 1H), 9.24 (s, 1H). MS (ESI) m/z 281 ([M−H]$^−$);

EXAMPLE 3

(3-hydroxyphenyl)(1-propyl-1H-indazol-3-yl)methanone

A mixture of [3-(benzyloxy)phenyl]-(1-propyl-1H-indazol-3-yl)methanol (0.067 g, 0.18 mmol.), ammonium formate (0.09 g, 1.17 mmol) and 10% palladium on carbon (0.09 g) in 10 mL ethanol was heated at reflux for 18 hours. The reaction was filtered (celite) and the cake washed with excess ethanol. The filtrate was concentrated in vacuo. The crude product was purified by HPLC [column: silica gel 150×12 mm (Biotage) at 10 mL/min with methyl-t-butyl ether/hexane, gradient elution, 1:9 to 1:1 over 15 min) to give the title compound (0.022 g) as a white solid.

$^1$H NMR (DMSO-d$_6$): δ 0.87 (t, 3H), 1.92 (m, 2H), 4.53 (t, 2H), 7.04 (m, 2H), 7.38 (m, 2H), 7.52 (t, 1H), 7.68 (d, 1H), 7.87 (d, 1H), 8.27 (d, 1H), 9.75 (s, 1H). MS (ESI) m/z 279 ([M−H]$^−$).

EXAMPLE 4

(1-cyclopentyl-1H-indazol-3-yl)(3-hydroxyphenyl)methanone

Step A: [3-(benzyloxy)phenyl](1-cyclopentyl-1H-indazol-3-yl)methanol

A solution of [3-(benzyloxy)phenyl](H-indazol-3-yl) methanol (0.20 g, 0.6 mmol) in 2 mL DMF was added in one portion sodium hydride (0.024 g, 0.6 mmol, 60% in oil). After the gas evolution ceased, cyclopentyl bromide (0.107 mL, 1.0 mmol) was added and the reaction was stirred at ambient to 50° C. overnight. The cool reaction mixture was partitioned with EtOAc and 1 N HCl. The organic phase was washed with brine and dried (Na$_2$SO$_4$). The resulting residue was purified by HPLC chromatography through silica gel (column: 150× 12 mm (Biotage) at 10 mL/min with methyl-t-butyl ether/ hexane, gradient elution, 1:9 to 1:1) to give 0.107 g of the title compound.

$^1$H NMR (DMSO-d$_6$): δ 1.67 (m, 2H), 1.87 (m, 2H), 1.99 (m, 2H), 2.08 (m, 2H), 5.05 (s, 2H), 6.0 (m, 1H), 6.04 (m, 1H), 6.83 (dd, 1H), 6.99 (m, 2H), 7.12 (s, 1H), 7.18 (t, 1H), 7.28 (m, 2H), 7.35 (m, 2H), 7.39 (m, 2H), 7.59 (m, 2H). MS (ESI) m/z 373 ([M+H]$^+$);

Step B: (1-cyclopentyl-1H-indazol-3-yl)(3-hydroxyphenyl)methanone

A mixture of [3-(benzyloxy)phenyl]-(1-cyclopentyl-1H-indazol-3-yl)methanol (0.11 g, 0.37 mmol.), ammonium formate (0.09 g, 1.17 mmol) and 10% palladium on carbon (0.09 g) in 10 mL ethanol was heated at reflux for 18 hours. The reaction was filtered (celite) and the cake washed with excess ethanol. The filtrate was concentrated in vacuo. The crude product was purified by HPLC [column: silica gel 150×12 mm (Biotage) at 10 mL/min with methyl-t-butyl ether/hexane, gradient elution, 1:9 to 1:1 over 15 min) to give the title compound (0.025 g) as a white solid.

$^1$H NMR (DMSO-d$_6$): δ 1.73 (m, 2H), 1.89 (m, 2H), 2.09 (m, 2H), 2.21 (m, 2H), 5.34 (m, 1H), 7.035 (m, 1H), 7.37 (m, 2H), 7.51 (m, 1H), 7.65 *(m, 1H), 7.72 (d, 1H), 7.88 (d, 1H), 8.27 (d, 1H), 9.74 (s, 1H). MS (ESI) m/z 307 ([M+H]$^+$); Anal. calcd for C$_{19}$H$_{18}$N$_2$O$_2$.0.25H$_2$O: C:73.41; H:6.00 N:9.01 Found: C:73.77; H:6.04 N:9.01.

EXAMPLE 5

(3-hydroxyphenyl)(1-isopropyl-1H-indazol-3-yl) methanone

Step A: [3-(benzyloxy)phenyl](1-isopropyl-1H-indazol-3-yl)methanol

A solution of [3-(benzyloxy)phenyl](H-indazol-3-yl) methanol (0.20 g, 0.6 mmol) in 2 mL DMF was added in one portion sodium hydride (0.024 g, 0.6 mmol, 60% in oil). After the gas evolution ceased, 2-iodopropane (0.10 mL, 1.0 mmol) was added and the reaction was stirred at ambient to 50° C. overnight. The cool reaction mixture was partitioned with EtOAc and 1 N HCl. The organic phase was washed with brine and dried (Na$_2$SO$_4$). The resulting residue was purified by HPLC chromatography through silica gel (column: 150× 12 mm (Biotage) at 10 mL/min with methyl-t-butyl ether/hexane, gradient elution, 1:9 to 1:1) to give 0.091 g of the title compound.

$^1$H NMR (DMSO-d$_6$): δ 1.46 (d, 6H), 4.92 (m, 1H), 5.05 (s, 2H), 6.01 (m, 1H), 6.05 (m, 1H), 6.83 (dd, 1H), 6.97 (m, 2H), 7.12 (s, 1H), 7.18 (t, 1H), 7.27 (m, 2H), 7.36 (m, 5H), 7.59 (t, 2H).7.36 (m, 2H), 7.51 (t, 1H), 7.67 (s, 1H), 7.72 (d, 1H), 7.89 (d, 1H) 8.27 (d, 1H), 9.74 (s, 1H). MS (ESI) m/z 373 ([M+H]$^+$);

Step B: (3-hydroxyphenyl)(1-isopropyl-1H-indazol-3-yl)methanone

A mixture of [3-(benzyloxy)phenyl]-(1-cyclopentyl-1H-indazol-3-yl)methanol (0.11 g, 0.19 mmol.), ammonium formate (0.071 g, 1.17 mmol) and 10% palladium on carbon (0.09 g) in 10 mL ethanol was heated at reflux for 18 hours. The reaction was filtered (celite) and the cake washed with excess ethanol. The filtrate was concentrated in vacuo. The crude product was purified by HPLC [column: silica gel 150×12 mm (Biotage) at 10 mL/min with methyl-t-butyl ether/hexane, gradient elution, 1:9 to 1:1 over 15 min) to give the title compound (0.020 g) as a white solid.

$^1$H NMR (DMSO-d$_6$): δ 1.56 (d, 6H), 5.18 (m, 1H), 7.04 (d, 1H), 7.36 (m, 2H), 7.51 (t, 1H), 7.67 (s, 1H), 7.72 (d, 1H), 7.89 (d, 1H) 8.27 (d, 1H), 9.74 (s, 1H). MS (ESI) m/z 281 ([M+H]$^+$).

EXAMPLE 6

3-[(1-cyclopentyl-1H-indazol-3-yl)methyl]phenol

A mixture of [3-(benzyloxy)phenyl](1-cyclopentyl-1H-indazol-3-yl)methanol (0.24 g, 0.6 mmol) and 10% palladium on carbon in ethanol/cyclohexene (3:1, v/v) was heated at reflux for 1 hour. The catalyst was filtered (celite) and the filtrate concentrated in vacuo to give 0.85 g of product as a white solid.

$^1$H NMR (DMSO-d$_6$): δ 1.68 (m, 2H), 1.87 (m, 2H), 2.01 (m, 2H), 2.08 (m, 2H), 4.15 (2H), 5.08 (m, 1H), 6.54 (dd, 1H), 6.62 (s, 1H), 6.71 (d, 1H), 7.03 (m, 3H), 7.30 (m, 2H), 7.52 (dd, 1H), 7.59 (d, 1H), 9.21 (s, 1H). MS (ESI) m/z 293 ([M+H]$^+$).

EXAMPLE 7

(4-hydroxyphenyl)[7-(trifluoromethyl)-1H-indazol-3-yl]methanone

Step A: [4-(benzyloxy)phenyl][7-(trifluoromethyl)-1H-indazol-3-yl]methanone

A solution of 3-bromo-7-trifluoroindazole (1.8 g, 9.3 mmol) in 50 mL THF was cooled to −78° C. and treated dropwise with n-butyllithium (5.8 mL, 9.3 mmol, 1.6M in hexanes). After the addition was complete, t-butyllithium (10.9 mL, 18.6 mmol, 1.7M in pentane) was added dropwise to the cooled solution. After the mixture was stirred at −78° C. for 15 minutes, N-Methoxy-N-methyl-4-benzyloxybenzamide (2.5 g, 9.3 mmol) was added in 1 portion. The cooling bath was removed and the solution was allowed to warm to ambient temperature. The reaction was quenched with 1N HCl and extracted with EtOAc. The organic phase was washed with brine and dried (Na$_2$SO$_4$). Removal of the solvent afforded the crude product which was purified by flash chromatography (silica gel, hexane-ethyl acetate, 3:2) to give the title compound, 1.0 g of a light yellow solid. mp 172° C.;

$^1$H NMR (DMSO-d$_6$): δ 5.24 (s, 2H), 7.205 (d, 2H), 7.35 (m, 1H), 7.41 (t, 2H), 7.49 (m, 3H), 7.89 (d, 1H), 8.33 (d, 2H), 8.57 (d, 1H), 14.42 (broad s, 1H). MS (ESI) m/z 397 ([M+H]$^+$); Anal. calcd for C$_{22}$H$_{15}$F$_3$N$_2$O$_2$: C:66.67; H:3.81 N:7.07 Found: C:66.56; H:3.52 N:7.01.

Step B: (4-hydroxyphenyl)[7-(trifluoromethyl)-1H-indazol-3-yl]methanone

A mixture of [4-(benzyloxy)phenyl](7-triflurormethyl-1H-indazol-3-yl)methanol (0.06 g, 0.15 mmol) and 10% palladium on carbon (0.06 g) in 10 mL ethanol/cyclohexene (3:1, v/v) was heated at reflux for 2 hours. The catalyst was filtered (celite) and the filtrate concentrated in vacuo to give 0.035 g of product as a white solid.

$^1$H NMR (DMSO-d$_6$): δ 6.92 (d, 2H), 7.48 (t, 1H), 7.87 (d, 1H), 8.25 (d, 2H), 8.54 (d, 1H), 10.4 (broad s, 1H), 14.4 (broad s, 1H). MS (ESI) m/z 304 ([M−H]$^-$).

EXAMPLE 8

[1-cyclopentyl-7-(trifluoromethyl)-1H-indazol-3-yl] (4-hydroxyphenyl)methanone

Step A: [4-(benzyloxy)phenyl][1-cyclopentyl-7-(trifluoromethyl)-1H-indazol-3-yl]methanone To a solution of [4-(benzyloxy)phenyl](7-trifluoromethyl-1H-indazol-3-yl)methanone (0.372 g, 0.94 mmol) in 3 mL DMF was added in one portion sodium hydride (0.044 g, 1.1 mmol, 60% in oil). After the gas evolution ceased, cyclopentyl bromide (0.118 mL, 1.1 mmol) was added and the reaction was stirred at ambient to 50° C. for 24 hours. The cool reaction mixture was partitioned with EtOAc and 1 N HCl. The organic phase was washed with brine and dried (Na$_2$SO$_4$).

The solvent was removed in vacuo. The resulting residue was purified by flash chromatography (silica gel, hexane-EtOAc, 9:1) to give 0.320 g of the title compound as a yellow solid.

$^1$H NMR (DMSO-d$_6$): δ 1.74 (m, 2H), 1.94 (m, 2H), 2.10 (m, 2H), 2.22 (m, 2H), 5.25 (s, 2H), 5.32 (m, 1H), 7.21 (d, 2H), 7.35 (m, 1H), 7.40 (t, 2H), 7.49 (d, 2H), 7.54 (t, 1H), 7.995 (d, 1H), 8.30 (d, 2H), 8.66 (d, 1H). MS (ESI) m/z 465 ([M+H]$^+$);

Step B: [1-cyclopentyl-7-(trifluoromethyl)-1H-indazol-3-yl](4-hydroxyphenyl)methanone A mixture of [4-(benzyloxy)phenyl][1-cyclopentyl-7-(trifluoromethyl)-1H-indazol-3-yl]methanone (0.13 g, 0.28 mmol) and 10% palladium on carbon(0.10 g) in 10 mL ethanol/cyclohexene (3:1, v/v) was heated at 70° C. for 0.5 hours. The catalyst was filtered (celite) and the filtrate concentrated in vacuo to give crude product. The residue was crystallized from Et$_2$O/hexane to give 0.085 g of product as a white solid (mp 225-226° C.).

$^1$H NMR (DMSO-d$_6$): δ 1.72 (m, 2H), 1.94 (m, 2H), 2.10 (m, 2H), 2.21 (m, 2H), 5.31 (m, 1H), 6.92 (d, 2H), 7.52 (t, 1H), 7.98 (d, 1H), 8.205 (d, 2H), 8.63 (d, 1H), 10.46 (broad s, 1H). MS (ESI) m/z 375 ([M+H]$^+$); MS (ESI) m/z 373 ([M–H]$^-$); Anal. calcd for C$_{20}$H$_{17}$F$_3$N$_2$O$_2$: C:64.17; H:4.58 N:7.48 Found: C:64.01 H:4.44 N:7.17.

EXAMPLE 9

(4-hydroxyphenyl)[1-isopropyl-7-(trifluoromethyl)-1H-indazol-3-yl]methanone

Step A: [4-(benzyloxy)phenyl][1-isopropyl-7-(trifluoromethyl)-1H-indazol-3-yl]methanone To a solution of [4-(benzyloxy)phenyl](7-trifluoromethyl-1H-indazol-3-yl)methanone (0.20 g, 0.5 mmol) in 3 mL DMF was added in one portion sodium hydride (0.020 g, 0.5 mmol, 60% in oil). After the gas evolution ceased, 2-iodopropane (0.075 mL, 0.75 mmol) was added and the reaction was stirred at ambient to 50° C. for 24 hours. The cool reaction mixture was partitioned with EtOAc and 1 N HCl. The organic phase was washed with brine and dried (Na$_2$SO$_4$). Removal of the solvent in vacuo provided 0.18 g of the title compound which was used directly in the following step.

$^1$H NMR (DMSO-d$_6$): δ 1.59 (d, 6H), 5.12 (m, 1H), 5.25 (s, 2H), 7.22 (d, 2H), 7.35 (m, 1H), 7.41 (t, 2H), 7.49 (m, 2H), 7.54 (t, 1H), 8.0 (d, 1H), 8.32 (d, 2H), 8.65 (d, 1H). MS (ESI) m/z 441 ([M+H]$^+$);

Step B: (4-hydroxyphenyl)[1-isopropyl-7-(trifluoromethyl)-1H-indazol-3-yl]methanone A mixture of [4-(benzyloxy)phenyl][1-isopropyl-7-(trifluoromethyl)-1H-indazol-3-yl]methanone (0.17 g, 0.38 mmol) and 10% palladium on carbon (0.10 g) in 10 mL ethanol/cyclohexene (3:1, v/v) was heated at 70° C. for 0.5 hours. The catalyst was filtered (celite) and the filtrate concentrated in vacuo to give crude product. The residue was crystallized from Et$_2$O/hexane to give 0.130 g of product as a white solid $^1$H NMR (DMSO-d$_6$): δ 1.58 (d, 6H), 5.12 (m, 1H), 6.94 (d, 2H), 7.52 (t, 1H), 7.98 (d, 1H), 8.23 (d, 2H), 8.62 (d, 1H). MS (ESI) m/z 349 ([M+H]$^+$).

EXAMPLE 10

(3-hydroxyphenyl)[7-(trifluoromethyl)-1H-indazol-3-yl]methanone

Step A: (3-methoxyphenyl)[7-(trifluoromethyl)-1H-indazol-3-yl]methanone

A solution of 3-bromo-7-trifluoroindazole(5.0 g, 18.8 mmol) in 50 mL THF was cooled to −78° C. and treated dropwise with n-butyllithium (11.8 mL, 18.8 mmol, 1.6M in hexanes). After the addition was complete, t-butyllithium (22.0 mL, 37.6 mmol, 1.7M in pentane) was added dropwise to the cooled solution. After the mixture was stirred at −78° C. for 15 minutes, N-Methoxy-N-methyl-3-methoxybenzamide (3.7 g, 18.9 mmol) was added in 1 portion. The cooling bath was removed and the solution was allowed to warm to ambient temperature. The reaction was quenched with 1N HCl and extracted with EtOAc. The organic phase was washed with brine and dried (Na$_2$SO$_4$). Removal of the solvent afforded the crude product which was purified by flash chromatography (silica gel, hexane-ethyl acetate, 9:1) to give the title compound, 1.2 g of a white solid.

$^1$H NMR (DMSO-d$_6$): δ 3.84 (s, 3H), 7.27 (d, 1H), 7.52 (m, 2H), 7.78 (s, 1H), 7.88 (m, 2H), 8.58 (d, 1H). MS (ESI) m/z 321 ([M+H]$^+$);

Step B: (3-hydroxyphenyl)[7-(trifluoromethyl)-1H-indazol-3-yl]methanone

A solution of (3-methoxyphenyl)[7-(trifluoromethyl)-1H-indazol-3-yl]methanone (0.03 g, 0.094 mmol) in 2 mL of CH$_2$Cl$_2$ containing 0.2 mL cyclohexene was cooled to −78° C. under an argon atmosphere. Boron tribromide (0.035 mL, 0.375 mmol) was added in one portion and the reaction mixture was allowed to warm to ambient temperature. The reaction was quenched by the careful addition of methanol. The reaction mixture was partitioned with EtOAc and 1 N HCl. The organic phase was washed with brine and dried (Na$_2$SO$_4$). The solvents were removed in vacuo and the residue purified by flash chromatography to give 0.02 g of the title compound.

$^1$H NMR (DMSO-d$_6$): δ 7.07 (dd, 1H), 7.37 (t, 1H), 7.53 (t, 1H), 7.62 (s, 1H), 7.70 (d, 1H), 7.91 (d, 1H), 8.57 (d, 1H), 9.79 (s, 1H). MS (ESI) m/z 305 ([M–H]$^-$).

EXAMPLE 11

(3-hydroxyphenyl)[1-propyl-7-(trifluoromethyl)-1H-indazol-3-yl]methanone

Step A: (3-methoxyphenyl)[1-propyl-7-(trifluoromethyl)-1H-indazol-3-yl]methanone To a solution of [3-(methoxy)phenyl](7-trifluoromethyl-1H-indazol-3-yl)methanone (0.27 g, 0.85 mmol) in 5 mL DMF was added in one portion sodium hydride (0.034 g, 0.85 mmol, 60% in oil). After the gas evolution ceased, 1-iodopropane (0.097 mL, 1.0 mmol) was added and the reaction was stirred at ambient to 50° C. for 24 hours. The cool reaction mixture was partitioned with EtOAc and 1 N HCl. The organic phase was washed with brine and dried (Na$_2$SO$_4$).

Removal of the solvent in vacuo afforded the crude product which was purified by flash chromatography (silica gel, hexane/EtOAC, 9:1) to give the title compound (0.262 g) as an oil. MS (ESI) m/z 363 ([M+H]$^+$);

Step B: (3-hydroxyphenyl)[1-propyl-7-(trifluoromethyl)-1H-indazol-3-yl]methanone A solution of (3-methoxyphenyl)[1-propyl-7-(trifluoromethyl)-1H-indazol-3-yl]methanone (0.24 g, 0.66 mmol) in 10 mL of $CH_2Cl_2$ containing 0.2 mL cyclohexene was cooled to −78° C. under an argon atmosphere. Boron tribromide (0.25 mL, 2.65 mmol) was added in one portion and the reaction mixture was allowed to warm to ambient temperature. The reaction was quenched by the careful addition of methanol. The reaction mixture was partitioned with EtOAc and 1 N HCl. The organic phase was washed with brine and dried ($Na_2SO_4$). The solvents were removed in vacuo and the residue purified by flash chromatography to give 0.077 g of the title compound (mp 118° C.) as a light yellow solid.

$^1$H NMR (DMSO-$d_6$): δ 0.94 (t, 3H), 1.95 (m, 2H), 4.53 (t, 2H), 6.93 (d, 2H), 7.53 (t, 1H), 7.99 (d, 1H), 8.23 (d, 2H), 8.625 (d, 1H), 10.47 (broad s, 1H). MS (ESI) m/z 348 ([M+H]$^+$); Anal. calcd for $C_{18}H_{15}F_3N_2O_2$: C:62.07; H:4.34 N:8.04 Found: C:61.84 H:4.29 N:7.72.

EXAMPLE 12

[1-cyclopentyl-7-(trifluoromethyl)-1H-indazol-3-yl](3-hydroxyphenyl)methanone

Step A: [1-cyclopentyl-7-(trifluoromethyl)-1H-indazol-3-yl](3-methoxyphenyl)methanone To a solution of [3-(methoxy)phenyl](7-trifluoromethyl-1H-indazol-3-yl)methanone (0.27 g, 0.85 mmol) in 5 mL DMF was added in one portion sodium hydride (0.034 g, 0.85 mmol, 60% in oil). After the gas evolution ceased, cyclopentyl bromide (0.107 mL, 1.0 mmol) was added and the reaction was stirred at ambient to 50° C. for 24 hours. The cool reaction mixture was partitioned with EtOAc and 1 N HCl. The organic phase was washed with brine and dried ($Na_2SO_4$). Removal of the solvent in vacuo afforded the crude product which was purified by flash chromatography (silica gel, hexane/EtOAC, 9:1) to give the title compound (0.250 g) as an oil.

$^1$H NMR (DMSO-$d_6$): δ 1.72 (m, 2H), 1.84 (m, 2H), 2.18 (m, 2H), 2.42 (m, 2H), 3.79 (s, 3H), 5.35 (m, 1H), 7.263 (dd, 1H), 7.51(t, 1H), 7.57 (t, 1H), 7.82 (m, 2H), 8.15 (d, 1H), 8.675 (d, 1H). MS (ESI) m/z 389 ([M+H]$^+$);

Step B: [1-cyclopentyl-7-(trifluoromethyl)-1H-indazol-3-yl](3-hydroxyphenyl)methanone A solution of [1-cyclopentyl-7-(trifluoromethyl)-1H-indazol-3-yl](3-methoxyphenyl)methanone (0.19 g, 0.49 mmol) in 10 mL of $CH_2Cl_2$ containing 0.2 mL cyclohexene was cooled to −78° C. under an argon atmosphere. Boron tribromide (0.185 mL, 1.95 mmol) was added in one portion and the reaction mixture was allowed to warm to ambient temperature. The reaction was quenched by the careful addition of methanol. The reaction mixture was partitioned with EtOAc and 1 N HCl. The organic phase was washed with brine and dried ($Na_2SO_4$). The solvents were removed in vacuo and the residue purified by flash chromatography to give 0.15 g of the title compound as a light yellow solid, (mp 152° C.).

$^1$H NMR (DMSO-$d_6$): δ 1.72 (m, 2H), 1.85 (m, 2H), 2.08 (m, 2H), 2.25 (m, 2H), 5.32 (m, 1H), 7.18 (dd, 1H), 7.38(t, 1H), 7.55 (t, 1H), 7.62 (s, 1H), 7.72 (d, 1H), 8.02 (d, 1H), 8.65 (d, 1H), 9.6 (s, 1H). MS (ESI) m/z 373 ([M−H]$^−$); Anal. calcd for $C_{20}H_{17}F_3N_2O_2 \cdot 0.25H_2O$: C :63.41 H:4.66 N:7.39 Found: C:63.48 H:4.53 N:6.91.

EXAMPLE 13

(3-hydroxyphenyl)[1-isopropyl-7-(trifluoromethyl)-1H-indazol-3-yl]methanone

Step A: [1-isopropyl-7-(trifluoromethyl)-1H-indazol-3-yl](3-methoxyphenyl)methanone To a solution of [3-(methoxy)phenyl](7-trifluoromethyl-1H-indazol-3-yl)methanone (0.27 g, 0.85 mmol) in 5 mL DMF was added in one portion sodium hydride (0.034 g, 0.85 mmol, 60% in oil). After the gas evolution ceased, 2-iodopropane (0.10 mL, 1.0 mmol) was added and the reaction was stirred at ambient to 50° C. for 24 hours. The cool reaction mixture was partitioned with EtOAc and 1 N HCl. The organic phase was washed with brine and dried ($Na_2SO_4$). Removal of the solvent in vacuo afforded the crude product which was purified by flash chromatography (silica gel, hexane/EtOAc, 9:1) to give the title compound (0.183 g) as an oil.

$^1$H NMR (DMSO-$d_6$): δ 1.58 (d, 6H), 5.12 (m, 1H), 7.18 (dd, 1H), 7.4 (t, 1H), 7.5 (t, 1H), 7.65 (s, 1H), 7.72 (d, 1H), 8.03 (d, 1H), 8.7 (d, 1H), 9.65 (s, 1H). MS (ESI) m/z 363 ([M+H]$^+$);

Step B: 3(-hydroxyphenyl)[1-isopropyl-7-(trifluoromethyl)-1H-indazol-3-yl]methanone A solution of [1-isopropyl-7-(trifluoromethyl)-1H-indazol-3-yl](3-methoxyphenyl)methanone (0.18 g, 0.5 mmol) in 10 mL of $CH_2Cl_2$ containing 0.2 mL cyclohexene was cooled to −78° C. under an argon atmosphere. Boron tribromide (0.188 mL, 2.0 mmol) was added in one portion and the reaction mixture was allowed to warm to ambient temperature. The reaction was quenched by the careful addition of methanol. The reaction mixture was partitioned with EtOAc and 1 N HCl. The organic phase was washed with brine and dried ($Na_2SO_4$). The solvents were removed in vacuo and the residue purified by flash chromatography (hexane/EtOAc, 2:1) to give 0.11 g of the title compound (mp 145° C.).

$^1$H NMR (DMSO-$d_6$): δ 1.58 (d, 6H), 5.12 (m, 1H), 7.18 (dd, 1H), 7.4 (t, 1H), 7.5 (t, 1H), 7.65 (s, 1H), 7.72 (d, 1H), 8.03 (d, 1H), 8.7 (d, 1H), 9.65 (s, 1H). MS (ESI) m/z 347 ([M−H]$^−$); Anal. calcd for $C_{18}H_{15}F_3N_2O_2$: C:62.07 H:4.34 N: 8.04 Found: C:61.83 H:4.18 N:7.91.

EXAMPLE 14

(3-hydroxyphenyl)[1-(2-methylprop-2-enyl)-1H-indazol-3-yl]methanone

Step A:
1H-indazol-3-yl(3-methoxyphenyl)methanone 1H-indazole-3-carboxylic acid methoxy methyl amide (18.1 g, 176.6 mmole) was dissolved in THF (97 mL). A 1M solution of 3-methoxyphenylmagnesium bromide in THF (194 mL, 0.194 mol) was added to the solution at room temperature.

The reaction was monitored by thin layer chromatography. When the reaction was complete, it was acidified with aqueous HCl, the THF was removed under reduced pressure, and extracted with ethyl acetate.

(1H-Indazole-3-yl)-(3-methoxyphenyl) methanone (19.39 g, 76.8 mmol) was crystallized as a white solid from ethyl acetate.

$^1$H NMR (DMSO-d$_6$): δ 3.82 (s, 3H), 723 (dd, 1H), 7.35 (t, 1H), 7.47 (m, 2H), 7.70 (d, 1H), 7.75 (m, 1H), 7.84 d, 1H), 8.27 (d, 1H).

Step B: (3-hydroxyphenyl)[1-(2-methylprop-2-enyl)-1H-indazol-3-yl]methanone (1H-Indazole-3-yl)-(3-methoxyphenyl) methanone (0.406 g, 1.6 mmol) was dissolved in DMF (5 mL) at room temperature. Sodium hydride 95% (0.045 g, 1.9 mmol) was added. When the evolution of hydrogen had stopped, bromo-2-methylpropene (0.324 mL, 3.2 mmol) was added. After the reaction stirred for several minutes, lithium chloride (3.41 g, 80.4 mmol) was added directly to the reaction mixture. The temperature was elevated to 160° C., and stirred for several days. The reaction was monitored my thin layer chromatography. When most of the starting material was gone, the reaction was diluted with water and ethyl acetate. The organic layer was repeatedly extracted with brine to remove DMF. The organic layer was passed through a pad of silica gel, then purified by flash chromatography (silica gel, hexane-EtOAc, 10:1 then 5:1), and crystallized with hexane to yield (3-hydroxyphenyl)[1-(2-methylprop-2-enyl)-1H-indazol-3-yl]methanone (0.160 g) as an off-white solid.

mp 75-78° C.

$^1$H NMR (DMSO-d$_6$): δ 1.63 (s, 3H), 4.63 (s, 1H), 4.88 (s, 1H), 5.14 (s, 1H), 7.00-7.02 (m, 1H), 7.35-7.37 (m, 2H), 7.46-7.50 (t, 1H), 7.54-7.55 (m, 1H), 7.63-7.66 (d, 1H), 7.76 (d, 1H), 8.24 (d, 1H) MS (ESI) m/z 291 ([M−H]$^−$).

EXAMPLE 15

{1-[(2E)-but-2-enyl]-1H-indazol-3-yl}(3-hydroxyphenyl)methanone (1H-Indazole-3-yl)-(3-methoxyphenyl) methanone (0.406 g, 1.6 mmol, example 14 step A) was dissolved in DMF (5 mL) at room temperature. Sodium hydride 95% (0.045 g, 1.9 mmol) was added. When the evolution of hydrogen had stopped, crotyl bromide (0.330 mL, 3.2 mmol) was added. After the reaction stirred for several minutes, lithium chloride (3.41 g, 80.4 mmol) was added directly to the reaction mixture. The temperature was elevated to 160° C., and stirred for several days. The reaction was monitored by thin layer chromatography. When most of the starting material was gone, the reaction was diluted with water and ethyl acetate. The organic layer was repeatedly extracted with brine to remove DMF. The organic layer was passed through a pad of silica gel, then purified by column chromatography, and crystallized with hexane to yield {1-[(2E)-but-2-enyl]-1H-indazol-3-yl}(3-hydroxyphenyl)methanone (0.163 g) as an off-white solid.

mp 75-78° C.; $^1$H NMR (DMSO-d$_6$): δ 1.94 (3H), 5.12 (s, 2H), 5.71-5.72 (m, 2H), 7.00-7.02 (m, 1H), 7.30-7.37 (m, 2H), 7.48-7.49 (m, 1H), 7.56-7.57 (m, 1H), 7.65-7.67 (m, 1H), 7.79 (d, 1H), 8.23 (d, 1H), 9.71 (s, 1H), MS (ESI) m/z 291 ([M−H]$^−$).

EXAMPLE 16

(3-hydroxyphenyl)[1-(3-methylbut-2-enyl)-1H-indazol-3-yl]methanone (1H-Indazole-3-yl)-(3-methoxyphenyl) methanone (0.406 g, 1.6 mmol, example 14 step A) was dissolved in DMF (5 mL) at room temperature. Sodium hydride 95% (0.045 g, 1.9 mmol) was added. When the evolution of hydrogen had stopped, 4-bromo-2-methyl-2-butene (0.371 mL, 3.2 mmol) was added. After the reaction stirred for several minutes, lithium chloride (3.41 g, 80.4 mmol) was added directly to the reaction mixture. The temperature was elevated to 160° C., and stirred for several days. The reaction was monitored by thin layer chromatography. When most of the starting material was gone, the reaction was diluted with water and ethyl acetate. The organic layer was repeatedly extracted with brine to remove DMF. The organic layer was passed through a pad of silica gel, then purified by column chromatography, and crystallized with hexane to yield (3-hydroxyphenyl)[1-(3-methylbut-2-enyl)-1H-indazol-3-yl]methanone (0.133 g) as an off-white solid.

mp 92-94° C.; $^1$H NMR (DMSO-d$_6$): δ 1.67 (s, 3H), 1.83 (s, 3H), 4.56-4.68 (m,1H), 5.14-5.16 (m, 2H), 5.38-5.40 (m, 1H), 7.00-7.02 (m, 1H), 7.30-7.36 (m, 2H), 7.46-7.50 (m, 1H), 7.57-7.62 (m, H), 7.64-7.68 (m, 1H), 7.73-7.75 (m, 1H), 8.21-8.24 (m, 1H), 9.70 (s, 1H) MS (ESI) m/z 307 ([M+H]$^+$).

EXAMPLE 17

(3-hydroxyphenyl)(1-isobutyl-1H-indazol-3-yl)methanone

Step A: 1H-Indazole-3-carboxylic acid methoxy-methyl-amide

Indazole-3-carboxylic acid (15 g, 0.0925 mol) was dissolved in DMF (40 mL) at room temperature. Carbonyldiimidazole (17 g, 0.104 mol) was added. A solution of diisopropylethylamine (18 mL, 0.104 mol) and N,O-dimethylhydroxylamine HCl (10 g, 0.104 mol) in DMF (10 mL) was added in portions. The reaction was stirred at room temperature overnight. The reaction was taken up in ethyl acetate and washed repeatedly with 2-N HCl, water, and brine. The organic layer was evaporated to a yellow oil, and passed through a pad of silica gel with hexane/ethyl acetate (1:2). The resulting solid was washed with ethyl acetate to give the desired product as a white solid (11.40 g, 0.056 mol).

Step B: (3-{[tert-butyl(diphenyl)silyl]oxy}phenyl)(1H-indazol-3-yl)methanone

Indazole-3-(N-methoxy-N-methyl)amide (0.0244 mol) and 1-Bromo-3-(tert-butyl diphenylsilyloxy)benzene (0.0244 mol) were dissolved in dry THF (144 mL, 0.17 M). The solution was vigorously stirred at −78 C. A solution of n-butyl lithium in hexane (2 equivalents of a 1.6 M solution, 0.0488 mol, 31 mL) was added very slowly (approximately 0.5 mL per minute). The reaction was stirred at −78 C for a half hour. The progress was monitored by TLC by quenching a small aliquot with 1-2 N aqueous HCl and eluting with ethyl acetate. In addition, the reaction was monitored with mass spec. When the reaction was complete, it was quenched with 1-2 N aqueous HCl and extracted with ethyl acetate. The product was purified by column chromatography. Hexane (100%) was used to remove the top spot, and hexane/ethyl acetate (50/50) was used to remove the product. The reaction gave 6.81 g (0.0143 mol, 59% yield) of product as a waxy solid. MS (ESI) m/z [M+H]+(477); MS (ESI) m/z [M−H]− (475);

Step C: [3-(tert-Butyl-diphenyl-silanyloxy)-phenyl]-(1-isobutyl-1H-indazol-3-yl)-methanone (3-{[tert-butyl(diphenyl)silyl]oxy}phenyl)(1H-indazol-3-yl)methanone (0.67 g, 0.0014 mol) was dissolved in DMF (10 mL). Sodium hydride (66%, 0.042 g, 0.0017 mol) was added, and the reaction was stirred until gas evolution stops. 1-iodo-2-methylpropane (0.242 mL, 0.0021 mol) was added. The reaction was stirred at room temperature overnight. The reaction is quenched with water and extracted with ethyl acetate. The desired product (0.650 g, 0.0012 mol, 87%) is isolated by chromatography with hexane/ethyl acetate (10:1).

Step D: (3-hydroxyphenyl)(1-isobutyl-1H-indazol-3-yl)methanone

[3-(tert-Butyl-diphenyl-silanyloxy)-phenyl]-(1-isobutyl-1H-indazol-3-yl)-methanone (0.650 g, 0.0012 mol) was dissolved in dry THF (1 mL) in a glass vial. The vial was cooled to −78 C in a dry ice/acetone bath. TBAF (1.8 mL of a 1 M soln., 0.0018 mol) was added. The vial was removed from the bath and stirred until a dark yellow color persisted (approx. 1 minute). The vial was placed back in the bath and the progress of the reaction was followed by TLC. When complete, the reaction was quenched with aqueous HCl (1-2N), adsorbed on a small plug of silica gel, and chromatographed with hexane/ethyl acetate (10:1) to give the desired product.

mp 108-110° C.; $^1$H NMR (400 MHz, DMSO-d$_6$): δ ppm 0.91 (d, J=6.66 Hz, 6H), 2.32 (m, 1H), 4.40 (d, J=7.17 Hz, 2H), 7.05 (m, 1H), 7.38 (m, 2H), 7.53 (t, J=8.46 Hz, 1H), 7.62 (m, 1H), 7.71 (m, 1H), 7.90 (d, J=8.59 Hz), 8.29 (dt, J=8.01, 0.99 Hz), 9.76 (s, 1H) MS (ESI) m/z 295 ([M+H]$^+$).

EXAMPLE 18

(1-allyl-1H-indazol-3-yl)(3-hydroxyphenyl)methanone

This compound was prepared in a method analogous to Example 17.
$^1$H NMR (400 MHz, DMSO-d$_6$): δ ppm 5.12 (d, J=1.41 Hz, 1H), 5.25 (m, 3H), 6.10 (m, 1H), 7.06 (m, 1H), 7.40 (m, 2H), 7.54 (t, J=8.33 Hz, 1H), 7.61 (m, 1H), 7.70 (m, 1H), 7.83 (d, J=8.58 Hz, 1H), 8.29 (dt, J=8.07, 1.03 Hz), 9.77 (s, 1H) MS (ESI) m/z 279 ([M+H]$^+$).

EXAMPLE 19

(1-benzyl-1H-indazol-3-yl)(3-hydroxyphenyl)methanone

This compound was prepared in a method analogous to Example 17.
$^1$H NMR (400 MHz, DMSO-d$_6$): δ ppm 5.85 (s, 2H), 7.07 (m, 1H), 7.33 (m, 7H), 7.52 (t, J=8.46 Hz, 1H), 7.64 (m, 1H), 7.73 (d, J=8.07 Hz, 1H), 7.87 (d, J=8.46 Hz, 1H), 8.29 (d, J=8.07 Hz, 1H), 9.78 (s, 1H) MS (ESI) m/z 329 ([M+H]$^+$).

EXAMPLE 20

(1-cyclohex-2-en-1-yl-1H-indazol-3-yl)(3-hydroxyphenyl)methanone

This compound was prepared in a method analogous to Example 17.

mp 140-141° C.; $^1$H NMR (400 MHz, DMSO-d$_6$): δ ppm 0.95 (broad m, 1H), 1.75-2.30 (broad m, 5H), 5.59 (m, 1H), 5.85 (m, 1H), 6.05 (m, 1H), 7.06 (m, 1H), 7.39 (m, 2H), 7.52 (m, 1H), 7.60 (m, 1H), 7.71 (dt, J=8.15, 1.42 Hz, 1H), 7.90 (d, J=8.53 Hz, 1H), 8.29 (d, J=8.02 Hz, 1H), 9.75 (s, 1H) MS (ESI) m/z 319 ([M+H]$^+$).

EXAMPLE 21

(3-hydroxyphenyl)[2-(3-methoxyphenyl)-2H-indazol-3-yl]methanone

Step A: (3-{[tert-butyl(diphenyl)silyl]oxy}phenyl)[2-(3-methoxyphenyl)-2H-indazol-3-yl]methanone To solution of (3-{[tert-butyl(diphenyl)silyl]oxy}phenyl)(1H-indazol-3-yl)methanone (0.10 g, 0.21 mmol)) in dry CH$_2$Cl$_2$ (4 mL) in a flame-dried flask was added dry pyridine (0.034 mL), anhydrous copper (II) acetate (0.057 g, 0.32 mmol), 3-methoxyphenylboronic acid (0.064 g, 0.42 mmol) and powdered 4 Angstrom molecular sieves (0.25 g). Stir at room temperature for seven days.

When complete, the entire reaction was adsorbed onto silica gel right from the flask, and purified by flash chromatography (hexane/ethyl acetate) to give the title compound. MS (ESI) m/z 583 ([M+H]$^+$).

Step B: (3-hydroxyphenyl)[2-(3-methoxyphenyl)-2H-indazol-3-yl]methanone

The silyl group was removed as described in example 17 step D to provide the title compound.
$^1$H NMR (400 MHz, DMSO-d$_6$): δ ppm 3.78 (s, 3H), 7.07 (m, 3H), 7.17 (m, 2H), 7.22-7.46 (m, 6H), 7.89 (d, J=8.71 Hz, 1H), 9.85 (s, 1H) MS (ESI) m/z 345 ([M+H]$^+$); MS (ESI) m/z 343 ([M−H]$^-$).

EXAMPLE 22

(3-hydroxyphenyl)[1-(3-methoxyphenyl)-1H-indazol-3-yl]methanone

This compound was prepared in a manner analogous to Example 21
$^1$H NMR (400 MHz, DMSO-d$_6$): δ ppm 3.88 (s, 3H), 7.08 (m, 1H), 7.14 (m, 1H), 7.40 (m, 2H), 7.41-7.53 (m, 3H), 7.59 (m, 1H), 7.71 (m, 1H), 7.77 (d, J=8.20 Hz, 1H), 7.94 (d, J=8.59 Hz, 1H), 8.39 (d, J=8.08 Hz, 1H), 9.82 (s, 1H) MS (ESI) m/z 345 ([M+H]$^+$); MS (ESI) m/z 343 ([M−H]$^-$).

EXAMPLE 23

[2-(4-bromophenyl)-2H-indazol-3-yl](3-hydroxyphenyl)methanone

This compound was made in a manner analogous to Example 22.

$^1$H NMR (400 MHz, DMSO-$d_6$): δ ppm 7.11 (m, 1H), 7.21 (m, 1H), 7.27 (m, 3H), 7.35 (m, 1H), 7.44 (m, 1H), 7.55 (d, J=8.84 Hz, 2H), 7.72 (d, J=8.84 Hz, 2H), 7.90 (d, J=8.71 Hz, 1H), 9.90 (s, 1H) MS (ESI) m/z 393/395 ([M+H]$^+$); MS (ESI) m/z 391/393 ([M−H]$^-$).

All patents, publications, and other documents cited herein are hereby incorporated by reference in their entirety.

-continued

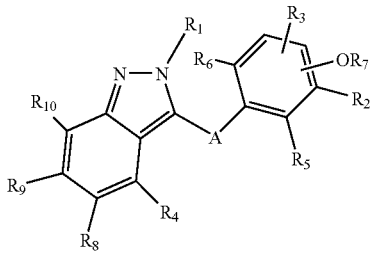

II

What is claimed is:

1. A compound of the formula I or II:

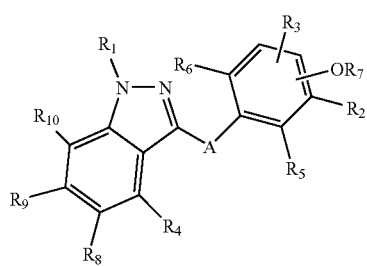

I an N-oxide thereof, or a pharmaceutically acceptable salt thereof, wherein:

A is (C=O), CHOH, C(OH)R, or CR'R";

R, R', and R" are each, independently, H, alkyl, aralkyl, or aryl;

$R_1$ is cycloalkyl, cycloalkenyl, or aryl;

$R_2$, $R_3$, $R_5$, and $R_6$ are each, independently, hydrogen, hydroxy, lower alkyl, alkoxy, or halogen;

$R_4$, $R_8$, $R_9$, and $R_{10}$ are each, independently, hydrogen, lower alkyl, hydroxy, alkoxy, aralkoxy, halogen, $CF_3$, aryl, aralkyl, heteroaryl or $COOR_{11}$;

$R_7$ is hydrogen, alkyl, —(C=O)$R_{16}$, —S(O)$_2R_{17}$, —S(O)$_2$N($R_{18}$)($R_{19}$), or D-glucuronidate;

$R_{11}$ is hydrogen, lower alkyl, aryl, or aralkyl;

$R_{16}$ is alkyl, aralkyl or aryl;

$R_{17}$ is alkyl, aryl, heteroaryl, cycloalkyl, alkenyl, cycloalkenyl, or alkynyl; and $R_{18}$ and $R_{19}$ are each, independently, hydrogen, alkyl, alkenyl, alkynyl, cycloalkyl, monofluoroalkyl, perfluoroalkyl, aryl, arylalkyl, cycloalkenyl, heteroaryl, heteroarylalkyl, hydroxy-$(C_2-C_6)$alkyl, alkoxyalkyl, alkylthioalkyl, carbonyl, acyl, alkoxycarbonyl, —C(O)NH$_2$, alkylaminocarbonyl, dialkylaminocarbonyl, alkylaminoalkyl, or dialkylaminoalkyl;

or $R_{18}$ and $R_{19}$ are taken together with the nitrogen atom to which they are attached to form a saturated, unsaturated or partially saturated $C_4$-$C_6$ carbon ring.

2. The compound of claim 1 that is of the formula:

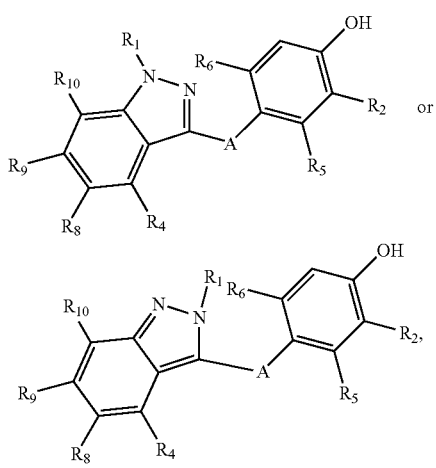

or an N-oxide thereof or a pharmaceutically acceptable salt thereof.

3. The compound of claim 1 that is of the formula:

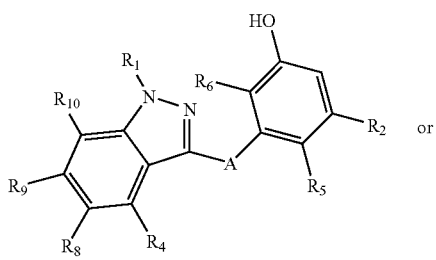

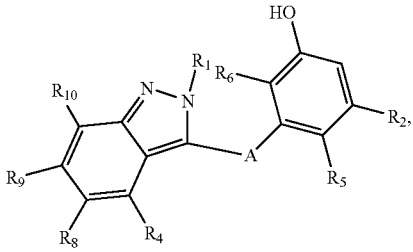

or an N-oxide thereof or a pharmaceutically acceptable salt thereof.

4. The compound of claim 1 that is formula I, or an N-oxide thereof or a pharmaceutically acceptable salt thereof.

5. The compound of claim 1 where $R_{10}$ is $CF_3$, or an N-oxide thereof or a pharmaceutically acceptable salt thereof.

6. The compound of claim 1 wherein $R_1$ is cycloalkyl or aryl, or an N-oxide thereof or a pharmaceutically acceptable salt thereof.

7. The compound of claim 1 that is formula II, or an N-oxide thereof or a pharmaceutically acceptable salt thereof.

8. The compound of claim 1 wherein the compound is:
(1-cyclopentyl-1H-indazol-3-yl)(3-hydroxyphenyl)methanone;
3-[(1-cyclopentyl-1H-indazol-3-yl)methyl]phenol;
[1-cyclopentyl-7-(trifluoromethyl)-1H-indazol-3-yl](4-hydroxyphenyl)methanone;
[1-cyclopentyl-7-(trifluoromethyl)-1H-indazol-3-yl](3-hydroxyphenyl)methanone;
(1-cyclohex-2-en-1-yl-1H-indazol-3-yl)(3-hydroxyphenyl)methanone;
(3-hydroxyphenyl)[2-(3-methoxyphenyl)-2H-indazol-3-yl]methanone;
(3-hydroxyphenyl)[1-(3-methoxyphenyl)-1H-indazol-3-yl]methanone; or
[2-(4-bromophenyl)-2H-indazol-3-yl](3-hydroxyphenyl)methanone,
or an N-oxide thereof or a pharmaceutically acceptable salt thereof.

9. A pharmaceutical composition comprising a compound of claim 1 or an N-oxide thereof or a pharmaceutically acceptable salt thereof, and a pharmaceutical carrier.

* * * * *

UNITED STATES PATENT AND TRADEMARK OFFICE
CERTIFICATE OF CORRECTION

PATENT NO.      : 7,598,286 B2                       Page 1 of 1
APPLICATION NO. : 11/260127
DATED           : October 6, 2009
INVENTOR(S)     : Steffan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 821 days.

Signed and Sealed this

Twenty-eighth Day of September, 2010

David J. Kappos
*Director of the United States Patent and Trademark Office*

SEQUENCE LISTING

```
<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 1
cacacggatg gcgcatact                                                  19

<210> SEQ ID NO 2
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 2
gaagtaccac gtagggctc                                                  19

<210> SEQ ID NO 3
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 3
cggcactggt ttccctcaca tgct                                            24
```